(12) United States Patent
Recht et al.

(10) Patent No.: US 11,655,443 B2
(45) Date of Patent: May 23, 2023

(54) THERMOCHROMIC SENSING DEVICES, SYSTEMS, AND METHODS

(71) Applicant: Palo Alto Research Center Incorporated, Palo Alto, CA (US)

(72) Inventors: Michael I. Recht, San Carlos, CA (US); Joerg Martini, San Francisco, CA (US); Peter Kiesel, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 17/733,076

(22) Filed: Apr. 29, 2022

(65) Prior Publication Data

US 2022/0259545 A1 Aug. 18, 2022

Related U.S. Application Data

(63) Continuation of application No. 14/984,719, filed on Dec. 30, 2015.

(51) Int. Cl.
| | |
|---|---|
| C12M 1/32 | (2006.01) |
| C12M 1/34 | (2006.01) |
| C12Q 1/18 | (2006.01) |
| C12Q 1/04 | (2006.01) |
| C12M 1/00 | (2006.01) |
| C12M 1/02 | (2006.01) |
| C12M 1/12 | (2006.01) |

(52) U.S. Cl.
CPC ............ *C12M 41/12* (2013.01); *C12M 23/12* (2013.01); *C12M 23/20* (2013.01); *C12M 31/00* (2013.01); *C12M 41/18* (2013.01); *C12Q 1/04* (2013.01); *C12Q 1/18* (2013.01); *C12M 25/14* (2013.01)

(58) Field of Classification Search
CPC . C12M 23/12; C12M 25/14; B01L 2300/0829
See application file for complete search history.

(56) References Cited

U.S. PATENT DOCUMENTS

| | | | |
|---|---|---|---|
| 3,561,269 | A | 2/1971 | Seitz |
| 3,813,554 | A | 5/1974 | Chang et al. |
| 6,160,617 | A | 12/2000 | Yang |
| 6,265,182 | B1 | 7/2001 | Kocagoz |

(Continued)

FOREIGN PATENT DOCUMENTS

| | | |
|---|---|---|
| EP | 1630532 | 3/2006 |
| WO | 2000024438 | 5/2000 |

(Continued)

OTHER PUBLICATIONS

Search Report for EP Appln No. 16204547.0, dated Apr. 7, 2017, 8 pgs.

(Continued)

*Primary Examiner* — Jonathan M Hurst
(74) *Attorney, Agent, or Firm* — Mueting Raasch Group

(57) ABSTRACT

A test vessel includes one or more test locations configured to contain a medium suitable for culturing a live substance. A thermochromic material is thermally coupled to the one or more test locations. The thermochromic material is configured to exhibit a spectral shift in light emanating from the thermochromic material in response to an increase or decrease in energy conversion by the live substance that causes a change in temperature of the thermochromic material.

20 Claims, 14 Drawing Sheets

(56) References Cited

U.S. PATENT DOCUMENTS

| | | |
|---|---|---|
| 6,660,345 B2 | 12/2003 | Coates et al. |
| 6,734,401 B2 | 5/2004 | Bedingham et al. |
| 7,094,595 B2 | 8/2006 | Cunningham et al. |
| 7,118,710 B2 | 10/2006 | Cunningham |
| 7,479,404 B2 | 1/2009 | Cunningham et al. |
| 7,701,590 B2 | 4/2010 | Kiesel et al. |
| 7,709,047 B2 | 5/2010 | Emmert-Buck et al. |
| 7,768,640 B2 | 8/2010 | Cunningham et al. |
| 7,784,173 B2 | 8/2010 | Wolkin et al. |
| 7,833,800 B2 | 11/2010 | Bell et al. |
| 8,182,430 B2 | 5/2012 | Short et al. |
| 8,393,785 B2 | 3/2013 | De Bruyker et al. |
| 8,594,470 B2 | 11/2013 | Kiesel et al. |
| 8,617,899 B2 | 12/2013 | De Bruyker et al. |
| 8,685,216 B2 | 4/2014 | De Bruyker et al. |
| 8,709,822 B2 | 4/2014 | Sun et al. |
| 9,341,444 B2 | 5/2016 | Levine et al. |
| 9,393,566 B2 | 7/2016 | Hasson et al. |
| 9,963,732 B2 | 5/2018 | Martini et al. |
| 9,994,889 B2 | 6/2018 | Tipgunlakant et al. |
| 10,106,839 B2 | 10/2018 | Hassibi |
| 10,598,554 B2 | 3/2020 | Kiesel et al. |
| 2002/0047003 A1 | 4/2002 | Bedingham |
| 2003/0052305 A1 | 3/2003 | Coates |
| 2007/0009968 A1 | 1/2007 | Cunningham et al. |
| 2007/0259598 A1 | 11/2007 | Ribi |
| 2008/0278722 A1 | 11/2008 | Cunningham et al. |
| 2009/0214804 A1 | 8/2009 | Levine et al. |
| 2009/0255535 A1 | 10/2009 | Kanzer |
| 2009/0318306 A1 | 12/2009 | Hasson et al. |
| 2010/0159610 A1 | 6/2010 | Sun et al. |
| 2010/0268112 A1 | 10/2010 | Short et al. |
| 2012/0312822 A1 | 12/2012 | Cheng et al. |
| 2013/0157376 A1 | 6/2013 | Nay |
| 2013/0225441 A1 | 8/2013 | Hassibi |
| 2013/0266977 A1 | 10/2013 | Mitchell et al. |
| 2014/0273191 A1 | 9/2014 | Tipgunlakant |
| 2014/0288381 A1 | 9/2014 | Faarbaek et al. |
| 2017/0191020 A1 | 7/2017 | Recht et al. |
| 2017/0191107 A1 | 7/2017 | Martini et al. |
| 2017/0191881 A1 | 7/2017 | Kiesel et al. |

FOREIGN PATENT DOCUMENTS

| | | |
|---|---|---|
| WO | 20080041146 | 4/2008 |
| WO | 20120094426 | 7/2012 |

OTHER PUBLICATIONS

Dybko et al., "Thermochomic compounds as transducers for fibre optic temperature probes," Opt Eng. Mar. 1, 2003;42(3):656-661.
File History for U.S. Appl. No. 14/984,754.
File History for U.S. Appl. No. 14/984,739.

THERMOCHROMIC SENSING DEVICES, SYSTEMS, AND METHODS

RELATED APPLICATIONS

This application is a continuation of U.S. Ser. No. 14/984,719 filed Dec. 30, 2015, which is incorporated herein by reference in its entirety.

TECHNICAL FIELD

This disclosure relates generally devices for analyzing substances using thermochromic sensing and to related systems and methods.

BACKGROUND

Susceptibility testing is performed to determine the effectiveness of a substance to inhibit the growth or cause the death of a live substance, e.g., bacteria, fungi, etc. In some cases, the goal of susceptibility testing is to predict the success or failure of antibiotic or other drug therapy. Tests are performed in a test vessel to determine the growth or lack thereof of a particular microbe to various drug types, drug combinations, and/or drug concentrations. Susceptibility testing is generally performed under controlled conditions and may be used to identify the most effective drug type, combination, and/or dosage to treat an infection caused by a particular type of bacteria, for example.

Susceptibility testing for antibiotic testing can involve growing a secondary culture of bacteria from a primary culture obtained from a patient. Currently, culturing the bacteria involves many replication cycles before a measurable effect of the drug being tested can be detected. It is desirable to shorten the time required for susceptibility testing so that an appropriate therapy can be quickly delivered to a patient.

BRIEF SUMMARY

Some embodiments are directed to a device comprising a test vessel having one or more test locations configured to contain a medium suitable for culturing a live substance. A thermochromic material is thermally coupled to the one or more test locations. The thermochromic material is configured to exhibit a spectral shift in light emanating from the thermochromic material in response to an increase or decrease in energy conversion by the live substance that causes a change in temperature of the thermochromic material.

In some embodiments, a test vessel, e.g., a test plate, includes one or more test wells configured to contain a medium suitable for culturing a live substance. A coating is thermally coupled to the test wells. The coating comprises a thermochromic material configured to exhibit a spectral shift in light emanating from the thermochromic material in response to an increase or decrease in energy conversion by the live substance, which causes a change in temperature of the thermochromic material.

Some embodiments are directed to a test kit, comprising a sterile test vessel having multiple test locations. A medium suitable for culturing a live substance is contained by the test vessel at the test locations. A thermochromic material is thermally coupled to the test locations. The thermochromic material is configured to exhibit a spectral shift in light emanating from the thermochromic material in response to an increase or decrease in energy conversion by the live substance that causes a change in temperature of the thermochromic material.

According to some embodiments a method includes providing a test vessel having one or more test locations configured to contain a medium suitable for culturing a live substance. A thermochromic material is disposed so that it is thermally coupled to the one or more test locations. The thermochromic material configured to exhibit a spectral shift in light emanating from the thermochromic material in response to an increase or decrease in energy conversion by the live substance which causes a change in temperature of the thermochromic material.

BRIEF DESCRIPTION OF DRAWINGS

The figures are not necessarily to scale. Like numbers used in the figures refer to like components. However, it will be understood that the use of a number to refer to a component in a given figure is not intended to limit the component in another figure labeled with the same number.

DETAILED DESCRIPTION OF ILLUSTRATIVE EMBODIMENTS

Figure 1:
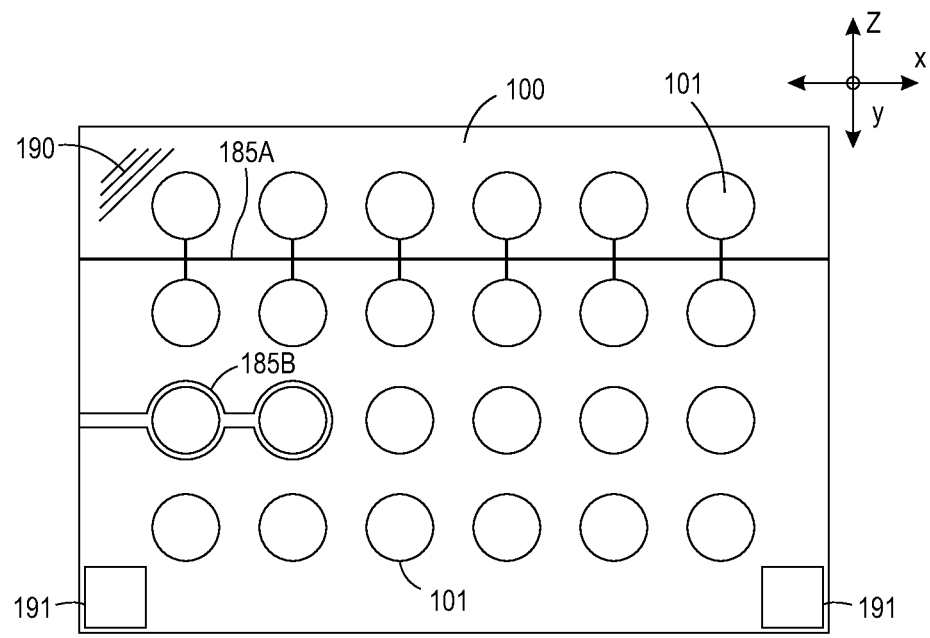
FIG. 1 is a plan view of a thermochromic sensing test vessel in accordance with some embodiments.

Thermochromism is the change in color of a material based on temperature. The color change of thermochromic materials can be relatively discrete and abrupt, or can vary gradually over a temperature range. The spectral changes may be evident in light that is scattered, reflected, absorbed, and/or fluoresces from the thermochromic material. Thermochromic materials may be organic or inorganic substances and/or may be monomers or polymers. Of particular interest for the approaches of the present disclosure are thermochromic liquid crystals, which exhibit thermochromism based on light reflectance.

The approaches described herein involve temperature sensing using thermochromic material to optically indicate temperature changes caused by energy conversion of a live substance. A non-limiting list of live substances that can be monitored using the thermochromic sensing techniques described herein include one or more of bacteria, archea, protists, fungi, plant cells, animal cells, viruses in appropriate host cells, phages in appropriate host cells, cancer cell cultures, and tissue cell cultures. The rate of energy conversion of the live substance can be related to the metabolism of the ensemble of live cells. In particular the number of cells increasing due to cell mitosis is a form of increase in ensemble metabolism. The metabolism of the individual cells combined comprises the ensemble metabolism. Metabolism often includes the oxidation of glucose or other carbohydrates to release energy and chemical byproducts. In this context metabolism is meant to be the mechanism through which chemical energy is converted into other forms of energy, including heat. Heat in turn can cause a temperature change of the substance or live matter that performs the metabolism. Temperature change of live matter will result in temperature change, normally a temperature increase, of the surrounding material including, cell culture medium, buffer material, vessel material and thermochromic material. The amount of heat transfer from one material to the next is dominated by material properties. Therefore, it is possible to control the heat transfer by material choice. It is desirable that the heat generated by metabolism is isolated from transfer into the vessel material and instead thermally connected or coupled to the thermochromic material. Heat generated by metabolism results preferably in a temperature change of the thermochromic material. An increase in ensemble metabolism can be described as "growth rate" of the live substance and/or to an increase or decrease in an amount of the live substance. A positive growth rate indicates healthy living condition for cells and it often corresponds to an increase in the number of live cells within the ensemble. The thermochromic sensing devices, systems, and methods disclosed herein can be used to detect and/or monitor growth of live substances and are particularly useful in determining the efficacy of various pharmaceutical agents, e.g., drug types, drug dosages, and drug combinations, such as anti-microbial, anti-viral, and/or anti-fungal drugs.

A spectral shift can occur in any kind of emission, absorption, fluorescence, reflection, or transmission, or any other light spectrum. A spectral shift in a light spectrum can be described as the difference between centroids of two light spectra. The wavelength shift may be determined by determining a measured centroid position with an implicit centroid position, determined in for example a calibration measurement or a nominal centroid position. The wavelength shift may be determined by comparing two different centroids of two different spectra effectively simultaneously to perform a referenced wavelength shift measurement. Light spectra, or light intensity spectra may be measured in various measurement unit. Commonly, the varying parameter of the spectrum (i.e. Abscissa) is the photon energy, often measured in wavelength. In such a measurement the wavelength shift can be measured in wavelength units, for example nanometers (nm). For certain emission spectra, in particular emission peaks or Gaussian emission profiles, the peak wavelength is a good approximation of the centroid position or the difference of peak positions relative to one another is a good approximation of wavelength shift. In practical measurements the centroid determination may be influenced by measurement parameters that may vary over the wavelength shift detection range so that there are additional measurement factors that are contributing to centroid measurements, for example wavelength dependent sensitivity of detectors. These measurement influences can be considered as systematic errors of the measurements and are often compensated for by calibration. Any such error, even if it is not compensated for, should be considered as part of the centroid, wavelength or wavelength shift measurement. It is noteworthy that emission spectra may consist of for example two relatively discrete emission distributions with two emission maxima. The centroid of these combined emission spectra can still be calculated and measured, a wavelength shift can still be calculated for such a spectrum. In particular, if two fluorescence emission spectra are used in such a way that one of the emission spectra changes the emission intensity with temperature then temperature changes result in a wavelength shift of the overall spectrum.

Figure 2:
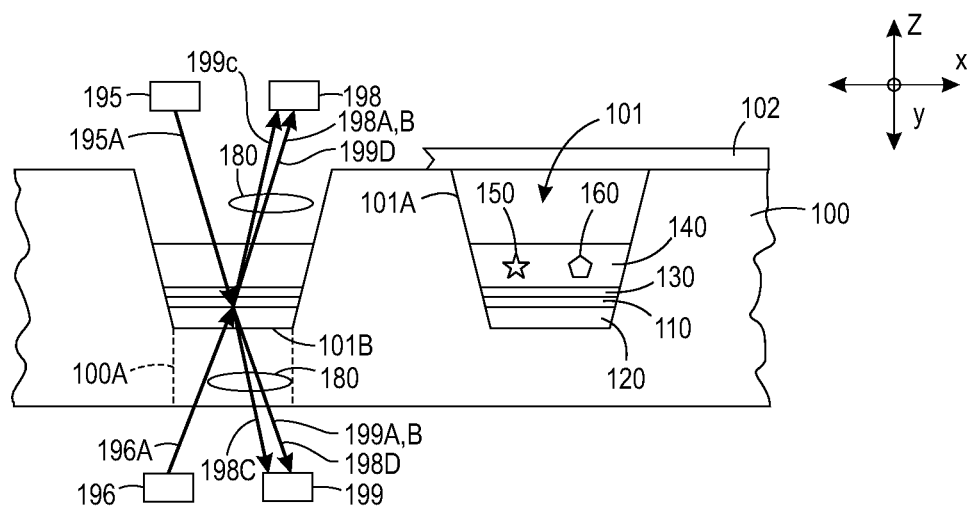
FIG. 2 is a cross sectional view of the test vessel of FIG. 1.

FIG. 1 and FIG. 2 are plan and cross sectional views, respectively, of a thermochromic sensing test vessel 100 in accordance with some embodiments. The test vessel 100 which may be a substantially planar test plate, includes one or more locations 101 configured to contain a medium 140 for culturing at least one live substance 150. In some embodiments, the test locations may be test wells which are recessed locations on a test plate, for example. Although the test vessel 100 may be any type of vessel or structure configured to contain a medium, in some implementations, the test vessel 100 is a MICROTITER test plate, such as a standard 24-well MICROTITER plate, a standard 96-well MICROTITER plate, a standard 384-well MICROTITER plate, or a standard 1536-well MICROTITER plate, etc. In implementations where the test vessel 100 is a test plate, the test wells of the test plate provide the locations 101 configured to contain the medium for culturing the live substance 150. Each test well has walls 101a and a bottom 101b to contain the medium 140. In some implementations, the test vessel 100 may include a cover 102 that covers the test wells and/or seals the medium within the test wells.

Although the test vessel 100 may be any type of vessel or structure configured to contain a medium, in some implementations, the test vessel 100 may maintain standard MICROTITER plate pitch distances for fluidic handling, such as a standard 24-well MICROTITER plate pitch distances, a standard 96-well MICROTITER plate pitch distances, a standard 384-well MICROTITER plate pitch distances, or a standard 1536-well MICROTITER plate pitch distances, etc. This could for example mean that test vessels could be loaded with standard MICROTITER fluidic handling tools (e.g. multiplexed pipettes) by using a compatible MICROTITER fluidic interface but the samples are afterwards routed into any other appropriate position that does not necessarily have to be compatible with the MICROTITER standard, for example a single row of test wells, for example 24, 96, 384, or 1536 wells.

At least one type of thermochromic material 110 is thermally coupled to the one or more test locations. In various embodiments, the thermochromic material may be disposed at the test locations, e.g., in, on, and/or about the test wells 101. The thermochromic material 110 is thermally coupled to the medium 140 and/or live substance 150 contained within the test locations. The thermochromic material 110 is configured and arranged so that it exhibits a spectral shift in light, e.g., scattered, reflected, or fluorescent light, from the thermochromic material 110 in response to a temperature change of the live substance 150 and/or medium 140 due to energy conversion by the live substance 150. The thermochromic material 110 is positioned to be sufficiently close and thermally coupled to the live substance 150 so as to be sensitive to changes in temperature due to energy conversion of the live substance 150.

At least one type of thermochromic material 190 is disposed near test locations, such that the thermochromic material 190 is thermally coupled to the surrounding environment of test wells 101. In some embodiments, the thermochromic material 190 is a coating of thermochromic material thermally coupled to the test locations, e.g., a thermochromic coating disposed at the bottom of the test wells.

At least one type of thermochromic material 191 is disposed on the test plate, in order to monitor a larger temperature range than the test wells. This temperature sensing region is not significantly influenced by the amount of energy conversion of the live substance in any of the test wells, rather it will track the temperature development of the test plate once the plate is moved into the incubator and the test plate temperature is approaching nominal temperature conditions. Additionally, proper incubator functioning can be tracked or controlled with this read out.

In individual locations 101 or the entirety of the test vessel 100 may be include a cover 102, which may comprise a lid and/or seal, e.g., sealing film. One type of sealing film is a breathable sterile membrane (e.g. Corning microplate sealing tape white Rayon (with acrylic) or Thermo Scientific Gas Permeable Adhesive Seals). This sealing film is placed directly on the test vessel 100 to provide a sterile barrier over which the cover 102 (for example, non-sterile plastic) can then be placed.

Another embodiment uses a sterile non-breathable adhesive seal (e.g. E&K Scientific SealPlate Adhesive Microplate Seals) as the lid 102 that covers the vessel. This type of film provides an air-tight seal and thus does not require another lid on top of the sealing film. For anaerobic bacteria, the cover 102 can be used to provide a barrier to exclude O2. Filling the test locations with media and using an air-tight seal will enable growth of anaerobic bacteria.

As illustrated in the cross sectional view of FIG. 2, the thermochromic material 110 may be a coating of thermochromic material 110 disposed along the walls 101a and/or bottom 101b of each individual test well 101. The thermochromic material may be a layer 111, e.g., a continuous layer, that extends across the test plate in x and y directions near the bottoms 101b of several test wells 101 as illustrated in the cross sectional view of FIG. 3.

The spectral shift in light emanating from the thermochromic material 110 (see FIG. 2), 111 (see FIG. 3), such as the spectral shift of the reflected, scattered, transmitted, and/or fluorescent light, can be detected using one or more optical detectors. The optical detectors may be located at any position relative to the test vessel where the light emanating from the thermochromic material is detectable. For example, in some embodiments, the detector may be positioned above, below, and/or along the walls 101a of the test wells 101.

In some embodiments, the reflected, scattered, transmitted, and/or fluorescent light emanating from the thermochromic material 110, is relayed onto the optical detector by appropriate optical components 180 such as lenses, objective lenses, lens combinations, imaging optics, plane-, concave-, convex-mirrors, fibers, gratings, prisms, and other elements. The optical components may maintain image information or not.

In some embodiments, the reflected, scattered, transmitted, and/or fluorescent light emanating from the thermochromic material 110 derives from measurement light that is ambient light, e.g., from sunlight, room light, etc., which encounters the thermochromic material 110, 111 and is scattered, transmitted, reflected or absorbed by the thermochromic material 110, 111. In some embodiments, at least one light source 195, 196 is used to emit and to direct the measurement light 195a, 196a toward the test wells 101 such that the measurement light 195a, 196a encounters the thermochromic material 110, 111.

Figure 3:
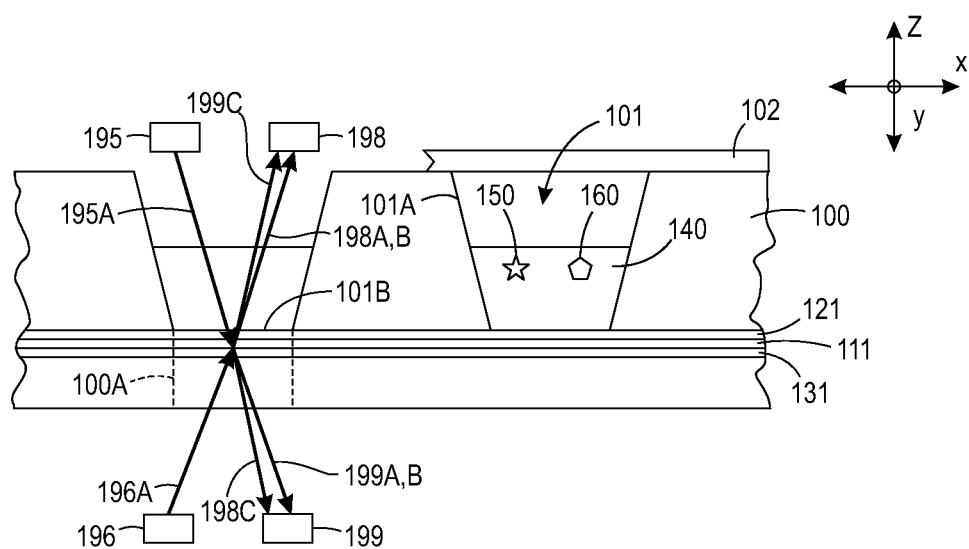
FIG. 3 is a cross sectional view of a test plate that includes a thermochromic material disposed in a layer that extends across the test plate in x and y directions near the bottoms of several test wells in accordance with some embodiments.

In some embodiments, the thermochromic material 110, 111 reflects a portion of the measurement light 195a, 196a. FIGS. 2 and 3 show reflected light 198a, 199a that can be detected by detectors 198, 199 positioned above and/or below the bottom of the test wells 101. In some embodiments, the thermochromic material 110, 111 absorbs a portion of the measurement light 195a, 196a, the absorption of the measurement light 195a, 196b causing the thermochromic material 110, 111 to fluoresce. FIGS. 2 and 3 indicate fluorescent light 198b, 199b that can be detected by one or more detectors 198, 199 positioned above and/or below the test wells 101. In some embodiments, a portion of the measurement light 195a, 196a is scattered by the thermochromic material 110, 111. The scattered light 198c, 199c can be detected by one or more detectors 198, 199 positioned above and/or below the test wells 101. In some embodiments, a portion of the measurement light 195a, 196a is transmitted by the thermochromic material 110, 111. The transmitted light 198d, 199d can be detected by one or more detectors 198, 199 positioned above and/or below the test wells 101. In some embodiments, the measurement light may be transmitted to the thermochromic material by a waveguide, e.g., an optical fiber or polymer waveguide. In some embodiments the reflected, scattered, transmitted or fluorescent light emanating from the thermochromic material may be transmitted to the detector through a waveguide. In some embodiments the waveguides may be integrally formed in the test vessel for transmitting measurement light and/or light emanating from the thermochromic material. In some embodiments the reflected, scattered, transmitted or fluorescent light emanating from the thermochromic material may be transmitted to the detector through a lens that is integral to the well plate structure, for example formed during the injection molding of the test plate.

In some embodiments, at least a portion 100a of the test plate 100 in the region of the test wells 101 is substantially optically transmissive at the wavelengths of the measurement light 196a and/or at the wavelengths of the reflected 199a, scattered 199b, transmitted 199d, and/or fluorescent light 198c emanating from the thermochromic material 110. Substantially optically transmissive means that the transmittance of light at the wavelengths of the measurement light and/or the light emanating from the thermochromic material is greater than 50%. In some embodiments the reflected, scattered, transmitted or fluorescent light emanating from the thermochromic material may be transmitted to the detector through a flat transparent bottom, for example glass, polypropylene, polystyrene, polycarbonate or quartz.

The energy conversion of the live substance results in a temperature increase of the thermochromic material at the test location. These temperature increases are sub-Kelvin, and may be less than about 1 milliKelvin (mK). Temperature changes may depend on a variety of factors, such as test volume, number of live cells, ambient temperature, thermal insulation of test volume, buffer conditions etc. As discussed herein, thermochromic materials can be used to optically indicate the temperature of the test vessels. Thermochromic materials can show a variety of optical effects such as temperature dependent fluorescence intensity or temperature dependent reflection or scattering spectra. In particular, thermochromic liquid crystals show very strong temperature dependent reflection spectra.

The thermochromic material used for thermochromic temperature sensing of the live substances may comprise any suitable type of thermochromic material such as thermochromic liquid crystals, leuco dyes, fluorophores, Prodan bound to DPPC, and/or fluorescent proteins. In thermochromic liquid crystals, the spectral changes result from temperature-dependent intermolecular spacing. For example, monitoring a specific selected reflectance from a thermochromic liquid crystal surface has shown up to a 13,000% change in intensity per K in a ratiometric color measurement or a wavelength shift of hundreds of nm/K up to about 1000 nm/K. 6-propionyl-2-(dimethylamino)naphthalene (Prodan) bound to ipalmitoylphosphatidylcholine (DPPC) shows a fluorescent emission shift of 6 nm/K between 40° C. and 50° C. Green fluorescence protein, which shows a shift in emission wavelength by about 0.3 nm/K, is an example of a thermochromic material that could be optimized genetically/biologically for thermochromic temperature sensing, e.g., optimized for pharmaceutical susceptibility testing and/or other monitoring of the growth/ decline of live substances.

Changes in fluorescence intensity of some thermochromic materials can be particularly sensitive to temperature (over 100% per degree in some cases). In some scenarios, thermochromic temperature sensing can be further enhanced by comparing the response of two different types of thermochromic materials with differing temperature responses and monitoring the change in intensity ratio between the two emission peaks from the two thermochromic materials. In some cases the two thermochromic materials are chosen such that one material shows a temperature dependent fluorescence intensity change, and the other is either independent of temperature, or has a change that is opposite to the first material.

As a non-limiting example, a thermochromic liquid crystal having a wavelength shift of about 1000 nm/K would exhibit a wavelength shift of about 10 picometer (pm) when subjected to a temperature change of about 10 pK due to energy conversion by a live substance. In some implementations, a $1.6 \times 10^{-6}$ K–$1.6 \times 10^{-5}$ K change in temperature due to energy conversion would result in a 1.6-16 picometer (pm) wavelength shift. In some embodiments, the thermochromic material may be configured to exhibit a spectral shift in the fluorescence, reflectance, or scattering spectrum with temperature in a range of about 0.5 nm/K to about 1000 nm/K.

In some configurations, one or more optional additional layers or coatings can be disposed along one or both major sides of the thermochromic material layer. In some embodiments, the optional additional layers may extend along the bottom 101b and/or walls 101a of the test wells 101. For example, one or more optional additional layers 120, 121, 130, 131 can be positioned between the thermochromic material coating 110, 111 and the medium 140 and/or live substance 150 within each test well 101, as shown in FIGS. 2 and 3. In some implementations, at least one of the optional additional layers 130 may be a light absorbing layer. The use of a light absorbing layer positioned between the thermochromic material 110, 111 and the medium 140 and/or live substance 150 can enhance sensitivity of the thermochromic sensing due to the absorbing properties of the layer. Light that is not reflected, scattered, absorbed by the thermochromic material coating 110, 111 now does not contribute to the reflected, scattered or fluorescence light detection. The use of a light blocking layer may enhance the signal to noise ratio of thermochromic sensing by reducing the component of the detector signal produced by non-signal light detected by the detector, wherein non-signal light is light other than light emanating from the thermochromic material.

In some implementations, at least one of the optional additional layers 130, 121 may be a heat conducting layer. The use of a heat conducting layer positioned between the thermochromic material 110, 111 and the medium 140 and/or live substance 150 can enhance sensitivity of the thermochromic sensing due to an improved heat conductivity from the medium 140 and/or live substance 150 to the thermochromic material coating 110, 111. Energy converted by the live substance 150 results in heat generation within the medium 140 and thereby in a temperature increase of the medium and/or live substance 150. A temperature difference between the medium and the ambient surrounding will result in a temperature gradient in the transition zone. As the thermochromic material is part of the transition zone, it is beneficial if a heat conducting layer ensures the heat transfer from the medium to the thermochromic layer so that both ideally have the same temperature. For example, the heat conducting layer may consist of indium tin oxide (ITO), metal, diamond, zinc oxide, graphene, graphite, and indium phosphide.

In some implementations, at least one of the optional additional layers 131, 120 may be a heat insulation layer. The use of a heat insulation layer positioned between the thermochromic material 110, 111 and the base material of the test vessel structure can enhance sensitivity of the thermochromic sensing due to reduced heat conductivity from the thermochromic material 110, 111 to the ambient equilibrium temperature. It is desirable to have the base material of the test vessel structure itself be made of low heat conductivity material.

In some embodiments, at least one of the optional additional layers 121, 130, may be a sterile coating positioned to separate the thermochromic material 110, 111 from the medium 140. For example, the thermochromic coating 110, 111 may be disposed along the bottom surface of the test wells with the sterile biocompatible coating disposed over the thermochromic coating so that the thermochromic coating is between the bottom surface of the test well and the sterile coating. For example, the sterile coating may comprise one or more of parylene, indium tin oxide (ITO), metal, polyethylene glycol (PEG), diamond, zinc oxide, graphene, graphite, and indium phosphide. Ideally these coatings are also biocompatible.

Figure 4:
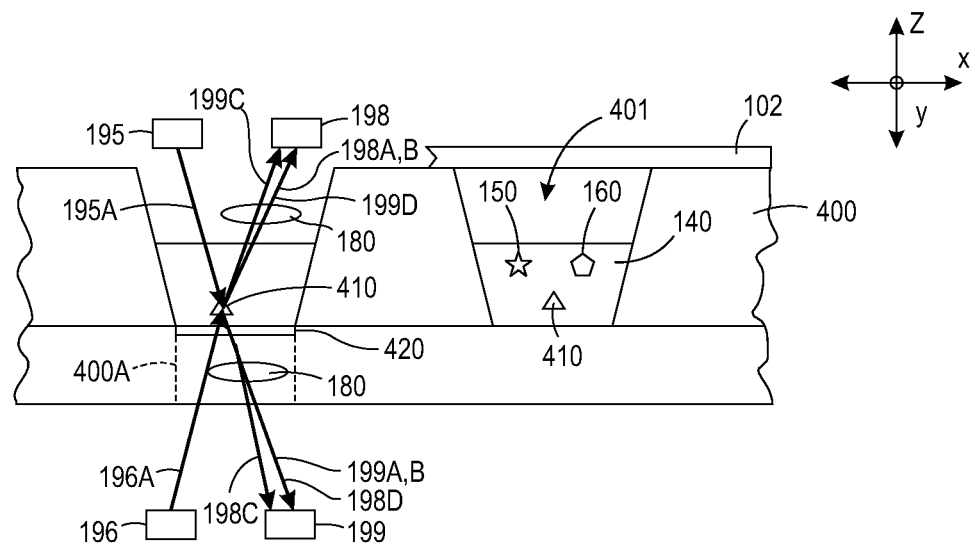
FIG. 4 is a cross sectional view of a test vessel comprising a number of locations configured to contain a medium for culturing at least one live substance with thermochromic material disposed within the test medium in accordance with some embodiments.

FIG. 4 illustrates a test vessel 400 comprising a number of locations 401 configured to contain a medium 140 for culturing at least one live substance 150. In some embodiments, the thermochromic material, e.g., thermochromic particles or regions 410, are disposed within the test medium 140 as depicted in the cross sectional diagram of FIG. 4.

The spectral shift in light emanating from the thermochromic material 410, such as the spectral shift of the reflected, scattered, transmitted, and/or fluorescent light, can be detected using one or more optical detectors. The optical detectors may be located at any position relative to the test vessel where the light emanating from the thermochromic material is detectable. For example, in some embodiments, the detector 198,199 may be positioned above and/or below the test wells 401 as illustrated in FIG. 4.

In some embodiments, the reflected, scattered, transmitted, and/or fluorescent light emanating from the thermochromic material derives from measurement light that is ambient light, e.g., from sunlight, room light, etc., which encounters the thermochromic material 410. In some embodiments, at least one light source 195, 196 is used to emit and to direct the measurement light 195a, 196a towards the test wells 401 such that the measurement light 195a, 196a encounters the thermochromic material 410.

In some embodiments, a portion of the measurement light 195a, 196a, is reflected by the thermochromic material 410. The reflected light 198a, 199a can be detected by photo sensing elements 198, 199 positioned above and/or below the bottom of the test wells 401.

In some embodiments, a portion of the measurement light 196a, 196a is absorbed by the thermochromic material 410 and causes the thermochromic material 410 to fluoresce. The fluorescent light 198b, 199b can be detected by one or more photo sensing elements 198, 199 positioned above and/or below the test wells 401.

In some embodiments, a portion of the measurement light 195a, 196a is scattered by the thermochromic material 410. The scattered light 198c, 199c can be detected by one or more photo sensing elements 198, 199 positioned above and/or below the test wells 401.

In some embodiments, at least a portion 400a of the test plate 400 in the region of the test wells 401 is substantially optically transmissive at the wavelengths of the measurement light 196a and at the wavelengths of the reflected 199a, scattered 199b, and/or fluorescent light 198c.

In some configurations, one or more optional additional layers or coatings 420 can be disposed along the bottom of the test well 401 or elsewhere, e.g., along the walls 401a of the test well 401. In some embodiments, the optional additional layers may extend both along the bottom 401b and walls 401a of the test wells 401. In some implementations, at least one of the optional additional layers 420 may be a heat insulating layer. The heat insulating layer can be designed to enhance sensitivity of the thermochromic sensing due to the reduced heat transfer from the test location 401 to the sacrificial material of the test vessel 400 or the surrounding.

In some implementations, at least one of the optional additional layers 420 may be a light blocking layer. The use of a light blocking layer may enhance the signal to noise ratio of thermochromic sensing by reducing the component of the detector signal produced by non-signal light, wherein non-signal light is light other than light emanating from the thermochromic material.

Figure 5:
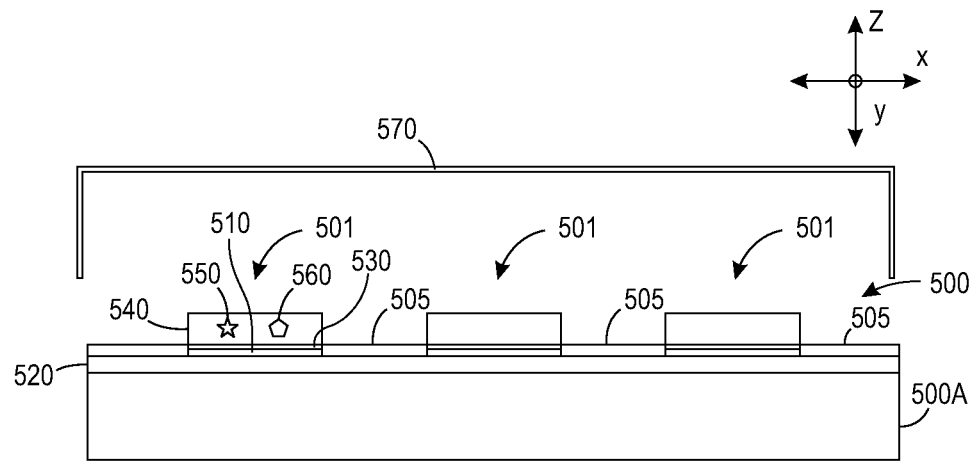
FIGS. 5 and 6 depict cross sectional diagrams of a test vessels that include locations that contain a medium suitable for culturing a live substance within an area on a relatively flat substrate in accordance with some embodiments.
Figure 6:
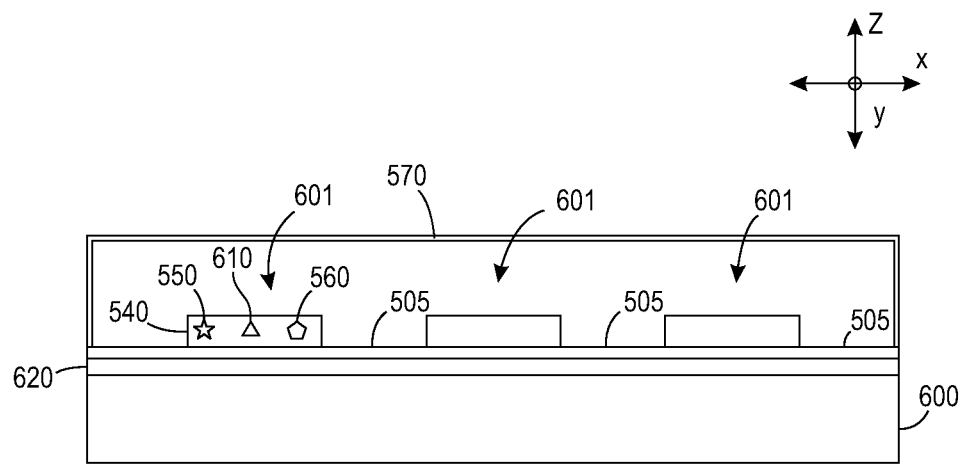

FIGS. 5 and 6 depict cross sectional diagrams of a test vessel 500, 600 that includes locations 501, 601 configured to contain a medium 540 suitable for culturing one or more live substances 560. In these embodiments, medium 540 may be contained within an area on a relatively flat substrate 500a. In some embodiments, the locations 501, 601 may be defined by surface treatments or coatings, 505, e.g., a hydrophobic surface treatment configured to contain the medium within the locations 501, 601. As shown in FIG. 5, the thermochromic material may be a layer 510 disposed on the substrate 500a at the locations 501.

In individual locations 501 or the entirety of the test vessel 500 may be covered with a cover 570, e.g., comprising a seal and/or lid. In some embodiments, the test vessel is covered with a sealing film with or without an additional lid. Some embodiments use a protective lid with or without a seal. The cover 570 reduces heat loss due to evaporation and helps to maintain an appropriate environment within the test vessel 500 at the test locations 501. For example, in some embodiments mammalian cells are disposed at the test locations which need a certain head volume that contains the appropriate gas atmosphere, e.g., 5% $CO_2$. As another example, anaerobic bacteria are disposed at the test locations and the cover provides a barrier that helps to exclude $O_2$ which is toxic to these bacteria. Thus, filling the test locations with media and using an air-tight seal enables the growth of anaerobic bacteria.

One type of seal is a breathable sterile membrane (e.g. Corning microplate sealing tape white Rayon (with acrylic) or Thermo Scientific Gas Permeable Adhesive Seals). This sealing film is placed directly on the test vessel to provide a sterile barrier over which the lid (for example, non-sterile plastic) can then be placed.

Another embodiment uses a sterile non-breathable adhesive seal (e.g. E&K Scientific SealPlate Adhesive Microplate Seals) to cover the vessel. This type of film provides an air-tight seal and thus does not require another lid on top of the sealing film unless the lid is desired or needed for additional protection.

As shown in FIG. 6, the thermochromic material may be thermochromic regions 610 within the medium 540, e.g., thermochromic particles embedded within the medium.

The test vessel 500, 600 may include one or more optional additional layers 520, 530, 620 disposed above and/or below the thermochromic material as discussed above. For example, the additional optional layers 520, 530, 620 may comprise one or more of a heat absorbing layer, a light blocking layer and a sterile biocompatible layer. Optionally, as discussed above, the test vessel includes a cover 570, e.g. a seal and/or lid.

Figure 7:
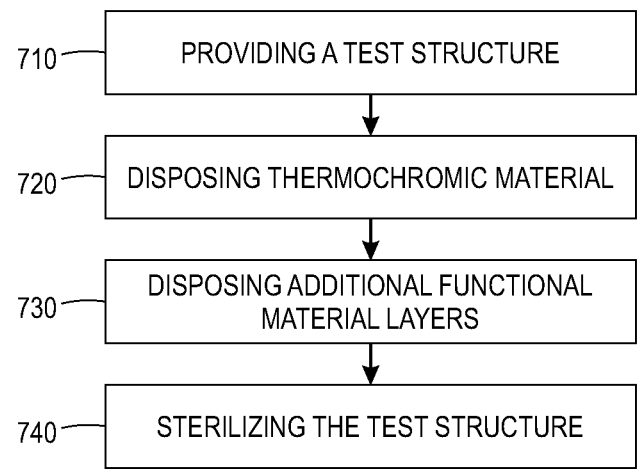
FIG. 7 is a flow diagram illustrating a process for making a thermochromic sensing test vessel in accordance with some embodiments.

FIG. 7 is a flow diagram illustrating a process for making a thermochromic sensing test vessel in accordance with some embodiments. The process includes providing 710 a test structure and disposing 720 a thermochromic material thermally coupled to test locations of the test structure. For example, in some embodiments, where the test structure is a standard MICROTITER test plate, the thermochromic material may be disposed by coating the test wells of the standard test plate with one or more thermochromic materials. For example, the bottom and/or walls of all of the test wells of a standard plate could be coated. In some embodiments the bottom and/or walls of some test wells may be coated with thermochromic material, whereas other test wells are left uncoated. In some embodiments, the thermochromic material may be disposed at the test locations by placing thermochromic particles into a medium contained by the test wells and/or by placing a medium that contains thermochromic material within the test wells.

In some embodiments additional functional material layers may be disposed 730 on the test structure, for example, heat conducting layers, light blocking layers, thermal insulation layers. The additional functional layers may be disposed before or after the thermochromic material is disposed at the test locations. Subsequently sterilizing the test structure 740 may be accomplished by one or more of the following methods: heat, chemicals, or irradiation.

Heat sterilization may be achieved using either moist heat (steam) or dry heat. Chemicals may be used to sterilize heat-sensitive materials including many plastics. Either gases or liquids may be used. Gases used for chemical sterilization include ethylene oxide (EtO), nitrogen dioxide ($NO_2$) or ozone. Liquid chemical sterilization may be achieved using glutaraldehyde, formaldehyde, hydrogen peroxide ($H_2O_2$), or peracetic acid. Radiation sterilization may be achieved using electron beams, X-rays, gamma rays, or irradiation by subatomic particles.

In some embodiments the sterilized test structure is packaged and sealed in such ways that the content of the package remains sterile until the mechanical integrity of the package is compromised, either inadvertently or deliberately. Normal deliberate opening maintains a sterile test plate and allows filling the test vessels exclusively with the live matter from the intended sample.

One or more test substances, e.g., a pharmaceutical, antimicrobial, antifungal substance, may be contained within the medium. Different locations of the test vessel, e.g., test wells 101 of the test vessel 100, may include different types, combinations, and/or concentrations of test substances 160 wherein the live substance 150 is the same at each test location. This test set up can be used to monitor the effect of the different types, combinations, and concentrations of the test substance on a live substance. In some embodiments the type, combination, and/or concentration of the test substance 160 may be substantially the same at a number of the test locations, and the live substance may vary. This test set up can be used to test the effect of the same type, combination, and concentration of the test substance on different types of live substances.

In some implementations, the thermochromic sensing test vessel is used for pharmaceutical, e.g., antimicrobial susceptibility testing (AST). The test substance 160 comprises one or more types of antibiotic and the test locations contain different types, different combinations, and/or different concentrations of antibiotic. Examples of antibiotics and combinations of antibiotics suitable for use in AST include, but are not limited to: Amikacin, Amoxicillin/Clavulanic Acid, Ampicillin, Ampicillin/Sulbactam, Azithromycin, Aztreonam, Cefalotin, Cefazolin, Cefepime, Cefoxitin, Ceftazidime, Ceftriaxone, Cefuroxime, Cephalothin, Chloramphenicol, Ciprofloxacin, Clarithromycin, Clindamycin, Daptomycin, Doripenem, Ertapenem, Erythromycin, Gatifloxacin, Gentamicin, Imipenem, Levofloxacin, Meropenem, Moxiflaxacin, Nalidixic Acid, Nitrofurantoin, Norfloxacin, Ofloxacin, Oxacillin, Penicillin, Piperacillin, Piperacillin/Tazobactam, Rifampin, Sulfamethoxazole, Synercid, Tetracycline, Ticarcillin, Ticarcillin/Clavulanic Acid, Tigecycline, Tobramycin, Trimethoprim, Trimethoprim/Sulfamethoxazole and Vancomycin.

Figure 8:
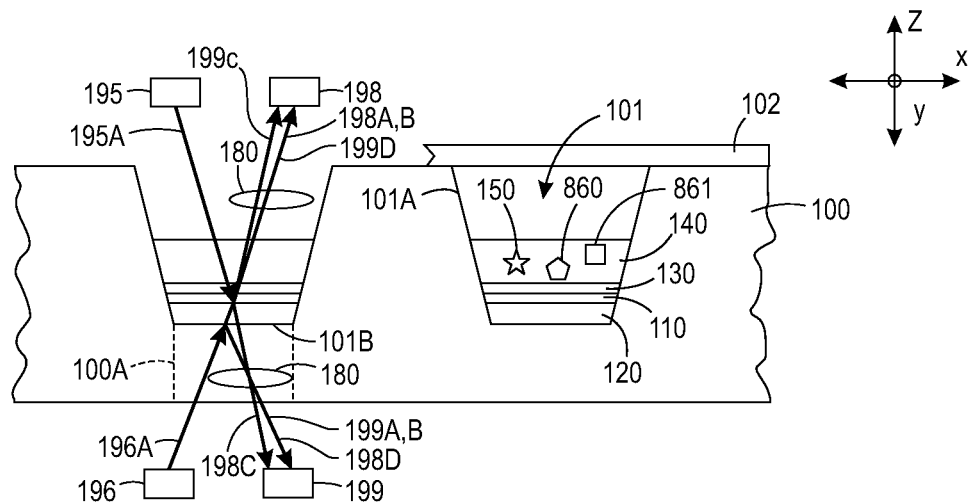
FIG. 8 is a cross sectional view of a thermochromic sensing test vessel configured for identification of a live substance.

In some implementations, illustrated by FIG. 8, the thermochromic sensing test vessel 100 is used for identification of the live substance 150. The test substance 860 comprises one or more types of substrates to measure carbon source utilization (e.g. mannitol, glucose, lactose, maltose, citrate, acetate, acetamide), enzymatic activity (e.g. catalase, oxidase, coagulase, pyrase, urease, decarboxylase, dihydrolase, phenylalanine deaminase, cysteine desulfurase (H2S production), tryptophanase (indole production)), or resistance (e.g. bacitracin, novobiocin, optochin). The growth medium may contain an indicator substance (861) in addition to the test substance 860. Examples of indicator substances include, but are not limited to: bromothymol blue, ferric ammonium citrate, bromocresol purple, ferric chloride, ferrous sulfate, 4-Dimethylaminobenzaldehyde, and methyl red. In some embodiments, the test substance 860 used for the identification of the live substance directly produces a fluorescent or chromogenic compound when incubated in the presence of the appropriate live substance 150.

In other embodiments, the indicator substance 861 produces a fluorescent or chromogenic compound when the test substance 860 is incubated in the presence of the appropriate live substance 150. In addition to measuring the response of the thermochromic material to the growth of the live substance in the presence of the test compound, the fluorescence or absorbance resulting from incubation of the live substance 150 in the presence of the test compound 860 can be measured using one or both of light sources 195,196 and using the detectors 198, 199 and/or additional light sources and/or detectors positioned above or below the test locations.

Combinations of enzyme substrates, growth promotors and growth inhibitors as measured by the TOAST mechanism or other optical means gives a metabolic or other biochemical profile that may be used for identification of live matter.

In cases of bloodstream infections, for example, the AST may be performed following isolation and identification of the live substance from a positive blood culture. The identification step may be performed a using the thermochromic sensing test vessel as described above. In other implementations, the live substance may be identified using another method such as standard growth and biochemical characteristics or rapid identification methods such as matrix-assisted laser desorption/ionization time-of-flight mass spectrometry (MALDI-TOF MS). In another implementation, the AST may be initiated prior to identification of the live substance, relying on the Gram stain results of the positive blood culture to select the appropriate panel of test compounds to use in the AST.

In some embodiments, the test vessel can be designed as a one-use disposable component. In some embodiments, the thermochromic sensing test vessel may be part of a kit that includes the sterile thermochromic sensing test vessel, e.g., as discussed in connection with FIGS. 1-6. In some implementations, the thermochromic sensing test vessel of the kit can be pre-loaded with medium and test substance. In some implementations the test substance comprises different types, amounts and/or combinations of pharmaceuticals or other agents that are preloaded at different test locations of a test vessel. In some scenarios, the test laboratory receiving the kit would insert the live substance at the test locations, test of the efficacy of the types, amounts and/or combinations of the test substance preloaded at each of the test locations, and then dispose of the kit after the testing is complete. In some cases, some of the test locations may be used as control locations, wherein the test substance and/or the live substance is not inserted at the control test locations.

Figure 9A:
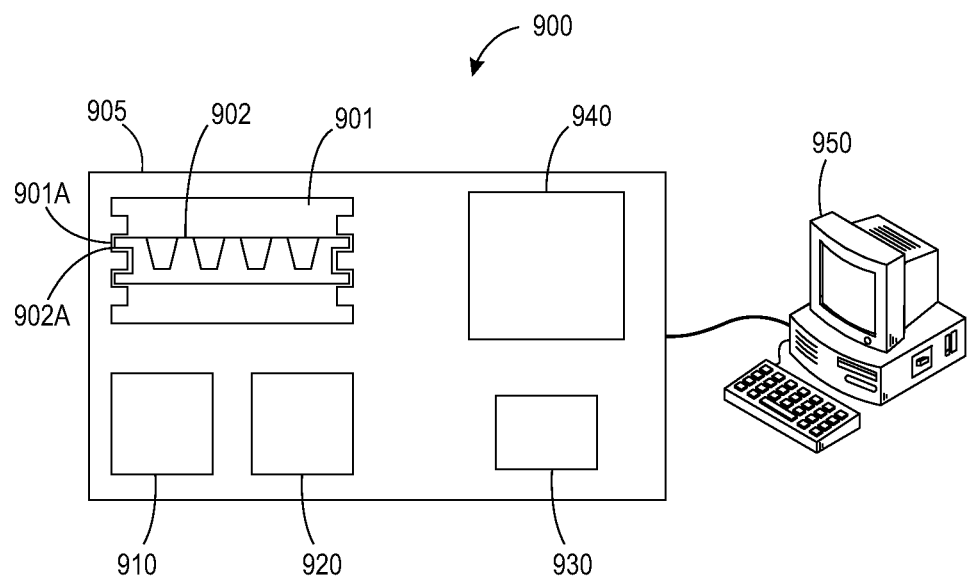
FIG. 9A shows a block diagram of a thermochromic temperature sensing test system in accordance with some embodiments.

The test vessel may be configured to be removably inserted into a compartment of a system that facilitates automatic testing of test substances using thermochromic sensing. In some implementations, the test vessel may be configured as a cartridge with mechanical holding features that engage with compatible features of the compartment. FIG. 9A shows a block diagram of a thermochromic temperature sensing test system 900 in accordance with some embodiments. In some embodiments the test system 900 includes an incubator 905 configured to automatically control the ambient environment, e.g., light, temperature, humidity, gas composition, $CO_2$ concentration, etc. of the test vessel 902 and/or other components of the system during testing. In test systems where the environment of the test vessel is uncontrolled or where additional thermal compensation is needed or desired, circuitry 930 configured to account for variation in temperature may be used. Temperature compensation circuitry 930 may comprise a temperature sensor coupled to compensation circuitry configured to compensate for temperature effects and therefore spectral shift of the thermochromic material that are caused by factors other than energy conversion by the live substance. These temperature effects may be caused by room temperature fluctuation and they may be larger than the maximum temperature measurement range of the optical temperature measurement range used for individual test wells 101. Therefore, the temperature of individual, groups of individual or all test wells can be adjusted with temperature compensation circuitry 930. Temperature compensation circuitry 930 may contain heaters, coolers, resistive heaters, radiative heaters, heat exchangers, water supply, thermoelectric coolers, Peltier elements, evaporative coolers, temperature sensors, thermistors, thermo couplers and optical temperature read out sensors that are based on wavelength shift detection of thermochromic material (for example 191 and 190).

In some embodiments the test vessel 902 includes fluidic channels 185b (shown in FIG. 1) fluidically coupled to the test locations 101 so that a thermally equilibrated liquid, e.g., predominantly water based, potentially with the addition of disinfectant agents, from the host incubation and read-out system 900 can be connected to the test vessel 902. The fluidic channels 185b can allow a fluid to be introduced into heat exchange regions of the test vessel near the test locations and/or control locations. Mass flow of the thermally equilibrated liquid into the test vessel 902 will bring the device temperature, including the content of the test sites 101 to a thermal equilibrium in a faster and more stable way than for example heat exchange by circulating gas or purely radiative heat exchange.

In some embodiments the test vessel 902 includes fluidic channels 185a (shown in FIG. 1) that fluidically coupled to the test locations 101 so that the test substance can be filled into several or all test location through these fluidic channels.

As indicated by FIG. 9A, the test vessel 902 can be configured as a cartridge that may be removably inserted into a compartment 901 of the test system 900. The test vessel 902 includes mechanical features 902a, e.g., protrusions, which engage with mechanical features 901a, e.g., slots, of the compartment to mechanically position and retain the test vessel 802 within the compartment 901. Additionally, the test vessel 902 can bear unique markings or identifiers that can be either read by humans, e.g. alphanumerical combinations, serial number or names, or by appropriate machines, e.g. bar codes or QR codes. The test vessel 902 can also be marked with alignment markings that define measurement test regions, for example a blue ring around each thermochromic material region 110 (see FIG. 2), 111 (see FIG. 3) for each test vessel 101, lines forming a coordinate system, alignment crosses in several positions on the test vessel. Especially, if a camera systems (RGB, differential illumination, hyperspectral, dichroic mirror multiplexed cameras, etc) serve as the multiplexed readout of thermochromic materials, the markings on the test vessel may indicate the regions of interest (ROI), i.e. the test locations 101 for automated readout. The markings may also imply the regions of interest by providing a coordinate system. The regions of interest would then be located at known, pre-defined coordinates.

The system 900 can include a measurement light source 910 configured to generate and direct measurement light toward the test locations of the test vessel 902. The light source 910 includes a light emitter, e.g., a light emitting diode (LED), a lamp, and/or laser, configured to emit the measurement light and components configured to cause the measurement light be directed to the test locations of the test vessel. In some implementations the measurement light is optically multiplexed or directed to the multiple test locations by scanning the measurement light across the test locations of the test vessel, for example by scanning mirrors or rotating mirrors or mirror arrays (digital light processing) or by acousto-optical modulators or by phased array optics. In some implementations, the measurement light scanning may be implemented by directing the light produced by a stationary measurement light emitter across multiple test locations, e.g., using a lens and/or mirror array. In some embodiments, scanning the measurement light across the test locations may be implemented by physically moving the light source and test vessel relative to each other. In some embodiments, the measurement light may be directed to the test locations through an optical waveguide. In some embodiments, the measurement light may reach a subset of test regions of interest or the measurement light may reach all test regions simultaneously, for example by illuminating the total area of all thermochromic material regions of the test vessel.

In some embodiments, the measurement light may include two or more distinct measurement light sources or measurement light characteristics that are individually addressable. For example two or more individually switchable LEDs that exhibit a different spectral emission characteristic could serve as measurement light sources. These light sources could alternatingly probe the reflectivity of a thermochromic liquid crystal in different spectral regimes. A light intensity detector, for example a monochrome camera, could then compare the intensity values of the reflected light spatially resolved for the light spectrum of the first LED and then for the light of the second LED. Thus, in some embodiments LEDs with very different spectral characteristics can be utilized with a monochrome light detector to measure wavelength shifts. Alternatively, a single broad light source (e.g. lamp, LED with phosphor coating, etc.) could be used to provide measurement light and the color discrimination of the reflected, transmitted, or scattered light could be performed with an RGB-camera. The spectral selectivity of RGB-cameras is aimed to represent the color selectivity of the human eye and the choices of color selectivity may therefore be limited when the RGB camera is used as the detector. In some embodiments color sensitive camera systems could be used that sequentially utilize light different filters (e.g. dielectric transmission filters, absorptive transmission filters), or camera systems could be used that use several image sensors and the incoming light is split by color selective elements such as dichroic mirrors as discussed below with reference to FIG. 9B.

The system 900 includes detector subsystem 920 including one or more optical detectors configured to detect changes in the spectrum of light emanating from the thermochromic material of the test vessel, e.g., reflected, scattered, and/or fluorescent light. The sensors may comprise one or more of a photodiode, a phototransistor, photomultiplier tube, avalanche photo diode, a wavelength shift detector, an RGB camera, a hyperspectral camera, a spectrometer, a spectrograph, a dichroic mirror segmented image sensor, a Fourier spectrometer, and a dichroic mirror segmented sensor. In some embodiments there may be a one-to-one correspondence between the sensors and the test locations. In other embodiments, there may be fewer sensors than test locations and light emanating from a plurality of the test locations is optically de-multiplexed to a single sensor. In some implementations, the optical de-multiplexing may be accomplished by selectively directing the emanating light from each of the plurality of test locations to the sensor during different time periods. e.g., de-multiplexing using moveable mirrors for example scanning mirrors or rotating mirrors or mirror arrays (digital light processing) or by acousto-optical modulators or by phased array optics. In some implementations, the optical multiplexing may be accomplished by physically moving the sensors relative to the test vessel and/or physically moving the test vessel relative to the sensors. The output of the detector subsystem 920 can be provided to an processor 940 configured to detect, analyze, and/or monitor changes in the spectrum of the emanating light. The processor 940 may be configured to analyze results of the testing, and/or to generate reports of the testing results into a format that can be displayed, sent or in any way transmitted to a user, e.g., via a computerized user interface 950. In some embodiments, the processor 940 may send continuous updates to the user interface 950 as the testing is being performed wherein the user interface continuously updates its display, allowing a user to be quickly apprised of testing results. In some implementations, the processor 940 may be configured to generate an alert signal that is sent to the user interface 950, wherein the user interface 950 produces an alert, e.g., an auditory and/or visual alert, based on the alert signal sent by the processor 940.

Figure 9B:
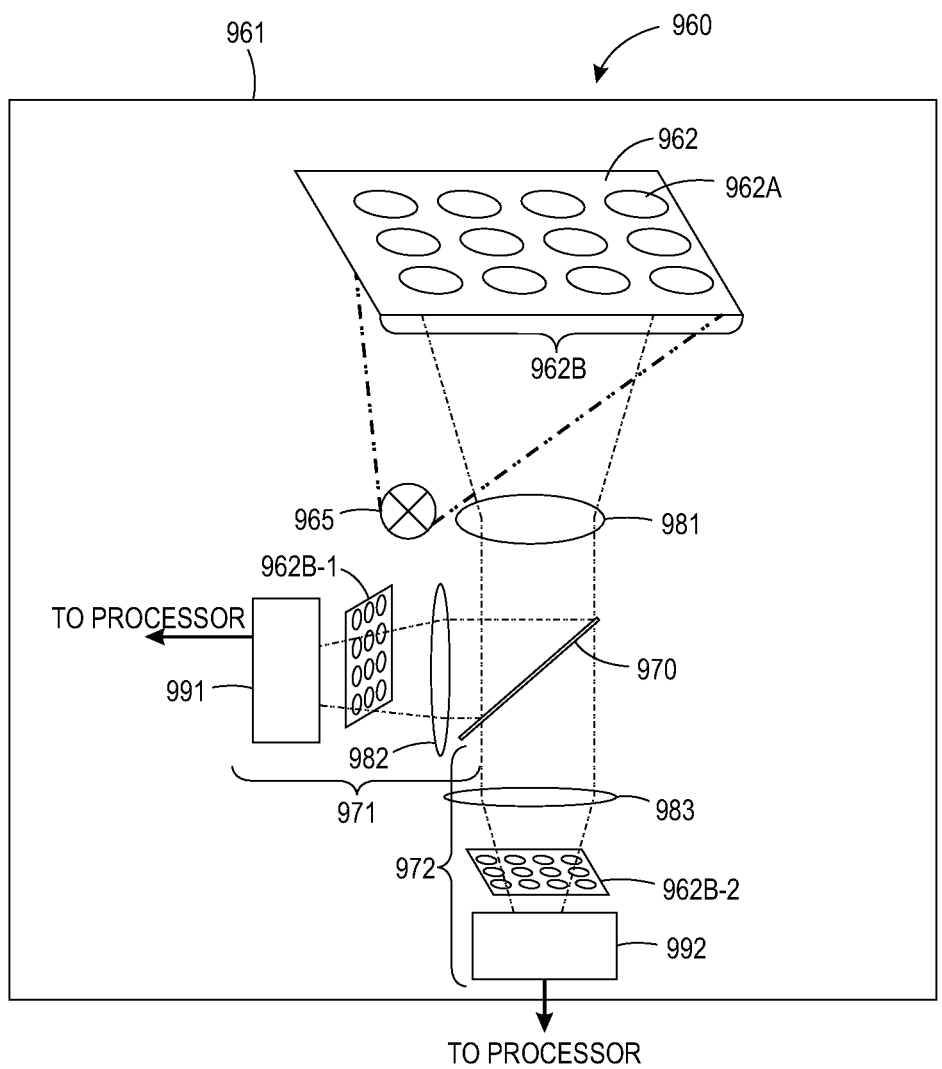
FIG. 9B shows a diagram of a portion of a thermochromic temperature sensing test system that includes two color channels in accordance with some embodiments.

FIG. 9B illustrates a portion 960 of the thermochromic temperature sensing test system 900 in accordance with some embodiments. The portion of the system illustrated in FIG. 9B includes two color channels 971, 972 that facilitate automatic testing of test substances according to some embodiments. In FIG. 9B, a test vessel 962 comprising multiple test locations 962a having thermochromic material disposed at the test locations 962a is shown disposed within an incubator 961. The incubator 961 controls the ambient environment of the test vessel 962. Measurement light is provided to the system 960 by a measurement light source 965 e.g., comprising one or more light emitting devices that provide broad band measurement light. Light from a spatial region 962b of the test vessel 962 is separated into two channels by a dichroic mirror 970. Imaging optics, e.g., lenses 981-983, may be disposed in the path of the light from the spatial region 962b, e.g., between the test vessel 962 and the dichroic mirror 970 and/or in one or both of the two color channels 971, 972. Lens 981 images the light from the spatial region 962b onto the dichroic mirror 970. The dichroic mirror 970 separates the light into two different color channels 971, 972, each color channel associated with a camera 991, 992. Each color channel 971, 972 provides an image 962b-1, 962b-2 of substantially the same spatial region 962b at different wavelengths. The dichroic mirror 970 has a center wavelength, $\lambda_{center}$, such that light having wavelengths greater than $\lambda_{center}$ are directed toward camera 991 in a first color channel 971 and light having wavelengths less than $\lambda_{center}$ are directed toward camera 992 in a second color channel 972.

If the images 962b-1, 962b-2 are not sufficiently identical, then translation, rotation or scaling transformations on the images 962b-1, 962b-2 can be used to overlay the images so that they represent substantially the same spatial region 962b. The images 962b-1, 962b-2 usually contain one, several or all test locations 962a and may include the thermochromic material disposed at the test locations 962a. In some embodiments the images 962b-1, 962b-2 include additional information such as markings. Additional markings may be identified by well-known techniques of computer vision and image processing and they may provide the system with operation parameters such as calibration data, patient data, mechanical alignment etc. Any relevant information contained in the markings can be processed in the system's processor 940 (see FIG. 9A). The images 962b-1, 962b-2 contain a representation of the different light intensities in the different wavelength regions for each image pixel.

In some embodiments the light emanating from thermochromic material at the spatial region 962b is included in the images 962b-1, 962b-2. In these embodiments, it is possible to generate temperature maps of the imaged region by calculating the wavelength shift for each pixel in the color images 962b-1, 962b-2. Groups of pixel may be combined into a region of interest (ROI) in a given image. Within a ROI the combination of pixels may for example be performed by the processor 940 by calculating the average intensity of pixel in the ROI, the sum intensity in the ROI, the median intensity in the ROI or any other mathematical operation based on the pixel values in the ROI to represent the intensity of the ROI. In some embodiments a ROI on the images substantially overlaps with a test location 962a. More than one ROI can be defined in each image, in particular each test location 962a in the image can be associated with at least one ROI. An ROI has at least two values associated with it. These two values represent the light intensities originating from the at least two color channels. A wavelength shift of an ROI may for example be calculated by subtracting the average values of the ROI in two color channels from another and dividing that value by the sum of the two ROI average values. In some embodiments a hyperspectral camera system is used to determine the wavelength shift of a ROI. In such a system, the peak intensity with respect to wavelength may be determined by finding the image of the wavelength region with the highest intensity in the ROI. It may be possible in such a scenario to extrapolate intensity values of the ROIs between color frames. In some embodiments a RGB camera system is used. The wavelength shift of an ROI may be calculated by omitting one of the three channels, for example the blue channel and treating the red and the green channels as the two channels described above. It may also be possible to add the red and green channel and treat this sum as a first color channel with the blue channel providing the second color channel as described above.

With camera based detection system there are several ways to determine a wavelength shift in a ROI as described above. In some embodiments the ROI can contain test locations 962a and thermochromic material is thermally coupled to the test locations. Therefore the wavelength shift of a ROI can be related to the temperature in that ROI and thereby the temperature of the test locations of the test vessel. Ideally, the camera system images all test locations and all positive and negative control locations in order to calculate the temperature development of the test locations over time and analyze it by comparing it to positive control location temperature developments over time.

Any of the above described system embodiments is suited to trace the temperature development of many locations on the test vessel by tracing local wavelength shifts on the vessel. Assuming that at least one thermochromic material is dispensed across the test plate at least in the relevant test locations and control locations, the local wavelength shift represents the local temperature on the plate.

Ambient temperature changes will affect the wavelength shift of the whole test plate, independent of temperature changes in/on the individual test locations. These ambient temperature changes are not necessarily homogeneous across the test plate. The temperature change of a test location can be referenced by the temperature change of an adjacent control location that does not contain any test substance and thereby serves as a test location for common mode rejection of ambient temperature fluctuations. It is noteworthy that the control location may surround the test location or may have a different size or shape than the test location. In particular the control location may not contain any live substance and therefore this control location serves as a negative control location that traces ambient temperature changes. By subtracting the temperature of the negative control location from the temperature of the test location at each measurement point in time, the temperature change of the test location is traced through time, to first order independent of ambient temperature changes. A positive control location contains living substance without any drug that could inhibit the metabolism of the live substance and its colony growth. In fact the system conditions such as nominal ambient temperature, ambient gas composition, etc. should be chosen to promote the growth of live substance. Positive control locations may be corrected for ambient temperature changes with readings from negative control locations in the same way that other test locations are corrected.

Figure 10A:
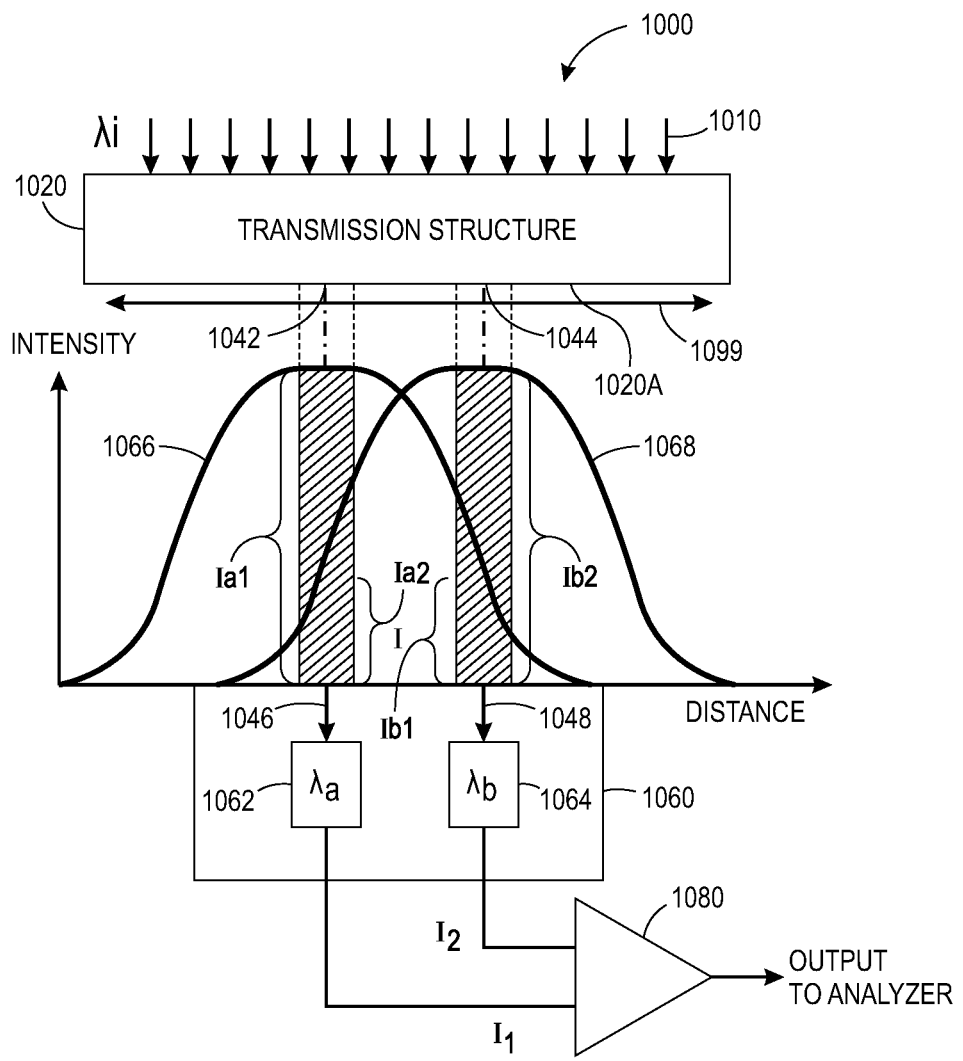
FIG. 10A conceptually illustrates a wavelength shift detector that can be used to determine the existence and/or amount of shift in the spectrum of light emanating from a thermochromic material in accordance with some embodiments.

FIG. 10A conceptually illustrates a wavelength shift detector 1000 that can be used as the detector subsystem 920 discussed in FIG. 9A to determine the center of a spectral distribution. Thereby the existence and/or amount of shift in spectrum of light, for example emanating from the thermochromic material, can be determined by comparing two or more center of spectral light distributions. Light 1010 emanating from the thermochromic material and characterized by a central wavelength $\lambda_i$ is input light to a spectrally varying optical transmission structure 1020. The transmission structure 1020 has a laterally varying transmission function such that the transmission function varies as a function of position along a lateral axis 1099 of its exit surface 1020a. The variation in transmission function can, for example, comprise a variation in intensity with wavelength according to a gradient, which can be a constant transmission gradient if it varies continuously and uniformly along the lateral axis 1099. The variation in transmission function can be spike-like transmission gradient if the intensity varies with wavelength in a step-like manner along the lateral axis 1099. More generally, light is described herein as transmitted with lateral variation when, in response to input light, transmitted light or output light varies with lateral position as a function of wavelength, and the variation with lateral position was not present in the input light. Variation with lateral position is illustrated in FIG. 10A by regions 1042 and 1044. As shown, region 1042 of the transmission structure 1020 transmits a sub-band of light in a subrange centered about wavelength $\lambda_a$. Similarly, region 1044 transmits a sub-band of light in a subrange centered about wavelength $\lambda_b$. As a result, the light from regions 1042 and 1044, represented respectively by rays 1046 and 1048, is incident on the photosensing component 1060 at different positions. Light characterized by central wavelength $\lambda_a$ is detected predominantly by the portion of the photosensing component 1060 at position 1062. Light characterized by central wavelength $\lambda_b$ is detected predominantly by the portion of the photosensing component 1060 at position 1064. If the central wavelength characterizing the input light 1010 is initially $\lambda_a$, a change in the wavelength of the input light to kb will causes a change in the position of light exiting the transmission structure 1020. This change in position will be indicated by a change in the light detected at positions 1062 and 1064 of the photosensing component 1060. More generally, a difference between the intensity of incident light at wavelengths $\lambda_a$ and $\lambda_b$ can be indicated by a difference in light detected at positions 1062 and 1064. A wavelength shift between wavelengths $\lambda_a$ and $\lambda_b$ or another change in wavelength distribution at the surface 1020a of transmission structure 1020 can change relative quantities of photons provided at positions 1062 and 1064, meaning that the quantities provided at the two positions have a different relation to each other after the change than they did before it. For example, the quantities could increase or decrease, but by amounts such that the quantity at one position becomes a larger or smaller fraction of the quantity at the other position; the quantity at one position could change from being less than the quantity at the other position to being greater; or one quantity could increase while the other decreases; etc. All of these types of changes could occur over time.

FIG. 10A shows the relationship between light intensity and position across the photosensing component 1060 in response to two different incident spectral patterns with light sub-bands having peak energy values. The first pattern, with peak intensity at wavelength $\lambda_a$, results in a light spot on the photosensing component 1060 that has an intensity distribution represented by curve 1066. The second distribution, with a peak intensity at wavelength $\lambda_b$, similarly results in a light spot with an intensity distribution represented by curve 1068. As will be understood, the first light spot, represented by curve 1066, may follow a continuous series of positions over time until it reaches the position of the second light spot, represented by curve 1068, if a light narrow band of input light 1010 from the transmission structure 1020 makes a continuous transition from $\lambda_a$ to $\lambda_b$.

The graph also shows quantities of photons sensed by positions 1062 and 1064 in response to the first and second light spots. When the first spot is provided on photosensing component 1060, position 1062 of the photosensing component 1060 generates a measurement quantity $I_1$ approximately proportional to the quantity of photons sensed by position 1062, namely $I_{a1}$, and generates a measurement quantity 12 approximately proportional to the quantity of photons sensed by position 1064, namely $I_{b1}$. $I_1$ and $I_2$ can, for example, be photocurrents generated by a position sensitive photo detector. When the second spot is on photosensing component 1060, position 1062 senses a quantity proportional to $I_{a2}$ and position 1064 senses a quantity proportional to $I_{b2}$. As will be seen, the relative quantities sensed by positions 1062 and 1064 change, with the first spot's relative quantity ($I_{a1}/I_{b1}$) being greater than unity and the second spot's relative quantity ($I_{a2}/I_{b2}$) being less than unity. Similarly, the difference ($I_{a1}-I_{b1}$) is a positive quantity whereas the difference ($I_{a2}-I_{b2}$) is a negative quantity. Furthermore, if a similar comparison is made with other adjacent or nearby positions, the peak intensity position of each spot can be approximated by finding the position on the photosensing component having the highest sensed quantity.

In some embodiments, the intensity of adjacent or overlapping spectral regions is integrated and compared to determine a wavelength shift in the distribution. The photosensing component 1060 may comprise two detectors and the integration over spectral regions can be performed by measuring the two adjacent regions 1062, 1064 using the two detectors, for example, photodiodes, split photodiodes, or photomultiplier tubes (PMT).

The spectrally varying transmission structure 1020 can comprise linear variable filters or spectrally dispersive elements (e.g., prisms, grating, etc.). For flexible measurements, stacked or multi-anode PMTs can be used on a spectrograph. The measurements may be performed at a frequency of at least about 0.01 Hz, up to at least about 1 MHz or even more. The combination of a laterally varying transmission structure 1020 and the position-sensitive photosensing component 1060 may resolve wavelength shifts significantly smaller than 10 femtometer (fm) or even smaller than 5 fm, e.g., about 3 fm. The individual photodiodes of the photosensing component 1060 can generate photo currents $I_1$ and $I_2$ that are amplified with a transimpedance amplifier 1080. Signal subtraction and addition may be performed with an analog circuit for superior noise performance prior to sampling by the analyzer. The center of the wavelength distribution can then be computed by $\lambda i \sim (I_1-I_2)/(I_1+I_2)$. In some embodiments, the total size of the wavelength shift detector 1000 can closely approach that of the photosensing component 1060, which is beneficial for mounting and long-term stability. Additional information involving the measurement of wavelength shifts in input light that can be used in conjunction with the thermochromic temperature sensing approaches disclosed herein is described in commonly owned U.S. Pat. No. 7,701,590 which is incorporated herein by reference.

Figure 10B:
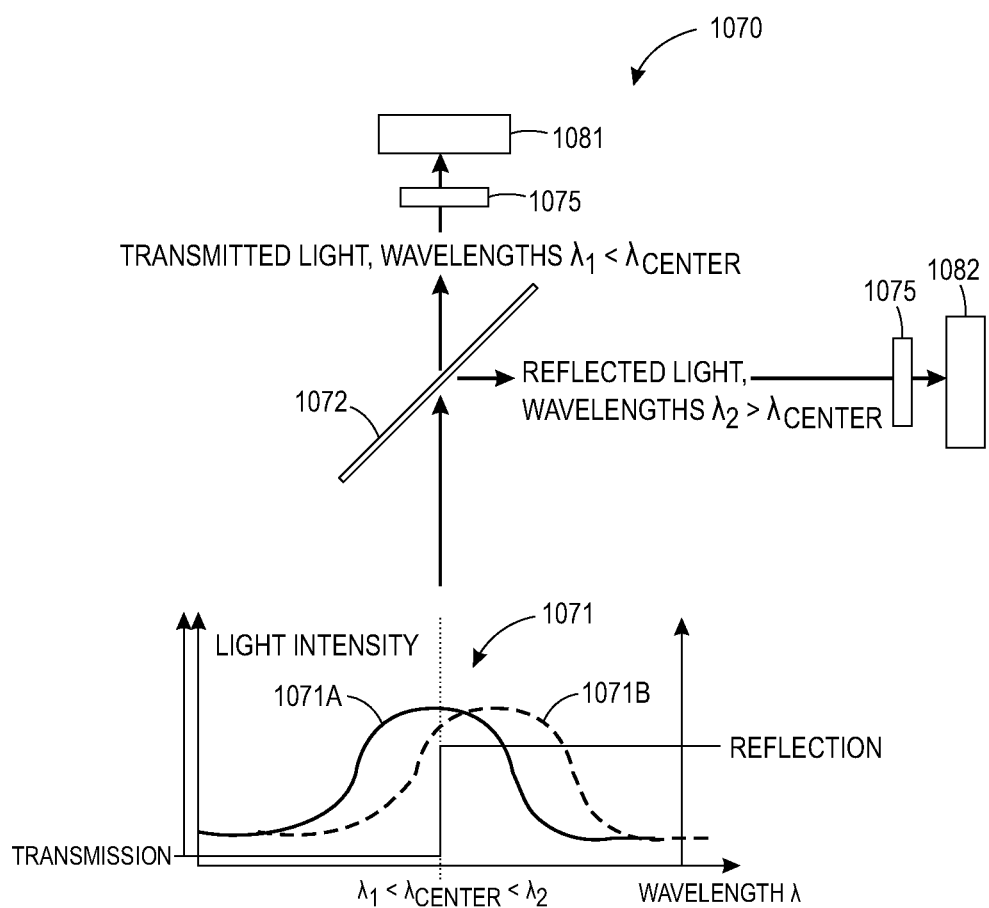
FIG. 10B conceptually illustrates a wavelength shift detector that detects both reflected and transmitted light in accordance with some embodiments.

FIG. 10B illustrates another embodiment of a spectral detector 1070. All wavelengths of light emanating 1071 from the thermochromic material (not shown in FIG. 10B) in response to measurement light are directed through a dichroic mirror 1072. The dichroic mirror 1072 reflects certain wavelength regions while transmitting other wavelength regions. For example the dichroic mirror 1072 could transmit all wavelength $\lambda_1 < \lambda_{center}$ and reflect all wavelength $\lambda_2 > \lambda_{center}$. Two different detectors, first detector 1081 and second detector 1082 are disposed to collect the transmitted and reflected light from the dichroic mirror 1072. Detector 1081 may be used to measure the total light intensity contained in the wavelength region that is smaller than the mirror's center wavelength $\lambda_{center}$ and detector 1082 may be used to measure the total light intensity contained in the wavelength region that is larger than the mirror's center wavelength $\lambda_{center}$. For a spectral distribution centered around the center wavelength, both measured light intensities would be identical (curve 1071a). For a spectral distribution that is shifted to longer wavelengths (curve 1071b), detector 1082 would measure higher light intensities than detector 1081. Therefore this detector used with the above-described method represents another way of detecting spectral light intensity distributions.

In some embodiments, additional optical elements 1075 may be introduced into the light detection path. For example, additional bandpass filters in front of the detectors 1081, 1082 may be used to limit the detected light to the spectral region that shows the largest shift for a given temperature change. In some embodiments, additional optical elements 1075 may include imaging lenses. Imaging may be particularly interesting, when the light detectors are image detectors, such as cameras. The full area of the complete test vessel may be illuminated and the measurement light from numerous test sites may be sensed simultaneously in a scheme as presented in FIG. 10B, by imaging the test vessel onto at least two cameras. For two simultaneously taken images the color distribution and therefore the temperature of all test locations can now be measured by measuring the recorded intensity of the appropriate pixels for each test location on both cameras. Additional markings on the test vessel may be used to identify the test locations in the images.

Figure 11A:
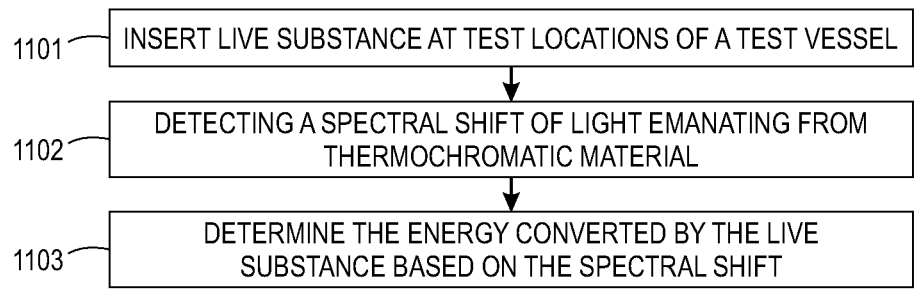
FIGS. 11A and 11B are flow diagrams illustrating a thermochromic testing process in accordance with some embodiments.

Thermochromic sensing may be used for a variety of testing protocols, such as testing the efficacy of various pharmaceuticals, e.g., antibiotics, antimicrobial agents, antifungal agents, cancer drugs, etc. The flow diagram of FIG. 11A illustrates a thermochromic testing process in accordance with some embodiments. The live substance is inserted 1101 into a medium disposed at test locations of a thermochromic test vessel. In some embodiments a test substance is also disposed in the medium. The live substance is thermally coupled to a thermochromic material located at the test locations. A spectral shift of light emanating from the thermochromic material is detected 1102. The spectral shift occurs in response to a temperature change caused by energy conversion by the live substance. The amount and/or rate of energy converted by the live substance may be determined 1103 based on the spectral shift. For example, in some implementations, live substance is a pathogen and the amount and/or rate of energy converted by the live substance indicates the susceptibility of the live substance to the test substance, e.g., an antibiotic. In some implementations, the live substance is a cell or tissue culture and the energy converted by the live substance can be related to mutations or other effects of the test substance on the cell or tissue culture.

As discussed above, thermochromic sensing is particularly useful for antibiotic or antimicrobial susceptibility testing. The goals of antimicrobial susceptibility testing are to detect possible drug resistance in pathogens and to assure susceptibility of the pathogens to drugs of choice for particular infections. Antimicrobial susceptibility testing may provide quantitative results, e.g., minimum inhibitory concentration of the antimicrobial test substance, and/or may provide qualitative assessment of efficacy of the test substance with respect to the pathogen. New and emerging mechanisms of resistance exhibited by many bacteria require vigilance regarding the ability of AST to accurately detect resistance. Particularly in view of these emerging mechanisms of resistance, it seems likely that phenotypic measures of the level of susceptibility of bacterial isolates to antimicrobial agents will continue to be clinically relevant for years to come.

AST measures the effect of drugs on the replication of microbes to determine which drug is best suited to kill the bacterium. AST may test many drugs in parallel in vitro to predict which drug works best in vivo. Thus, AST may test a broad sample of drugs so that the treatment choice can be targeted to the most effective antimicrobial drug for the particular bacteria.

Figure 11B:
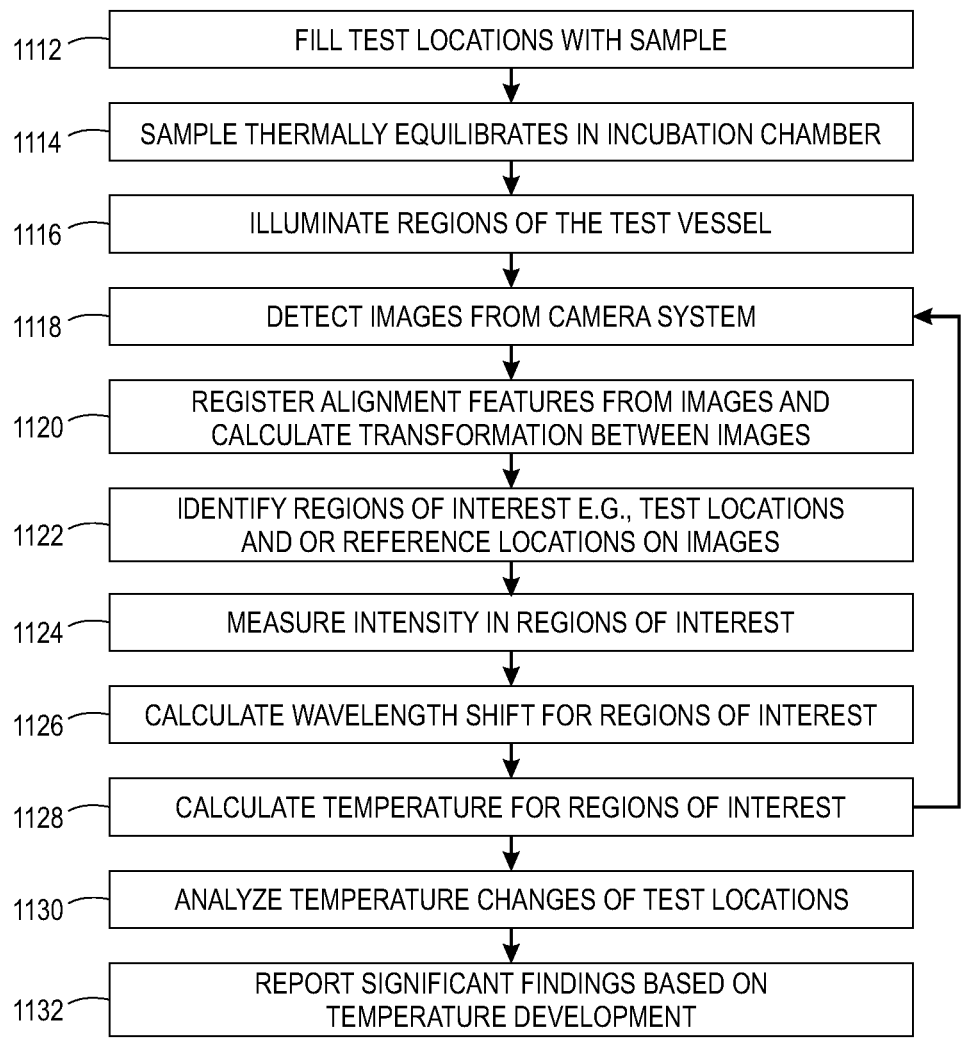

FIG. 11B is a flow diagram that illustrates a testing process in accordance with some embodiments. Test locations of a thermochromic sensing test vessel are filled with a sample 1112. The sample may include one or more of a medium, a live substance, a substance to be tested, e.g., antibiotic, and, in some embodiments, a thermochromic material. The sample and other structures near the sample, e.g. test locations and control locations, are thermally equilibrated 1114 in an incubation chamber. One or more regions of the test vessel that include test locations and control locations are illuminated 1116 with measurement light. Images of the regions are detected 1118 by a camera system. In some implementations, multiple images of the regions are detected and alignment features of the images are registered 1120 to align the images. A transformation between the images is calculated based on the alignment. Regions of interest within the images are identified 1122. For example, the regions of interest may include test locations and/or positive and/or negative reference control locations. The light intensity 1124 and wavelength shift 1126 of the regions of interest in the images are determined. The temperatures for the regions of interest are determined 1128, including determining the temperatures of the test locations and the positive and/or negative control locations. The process indicated by steps 1118 through 1128 is repeated until the conclusion of the test. The temperature changes in the region of interest are analyzed 1130. Any significant findings based on the temperature changes are reported 1132. In some embodiments, registration of the alignment features and calculation of the transformation between images may be performed once and used for the test, rather than being performed during each measurement loop.

Figure 12A:
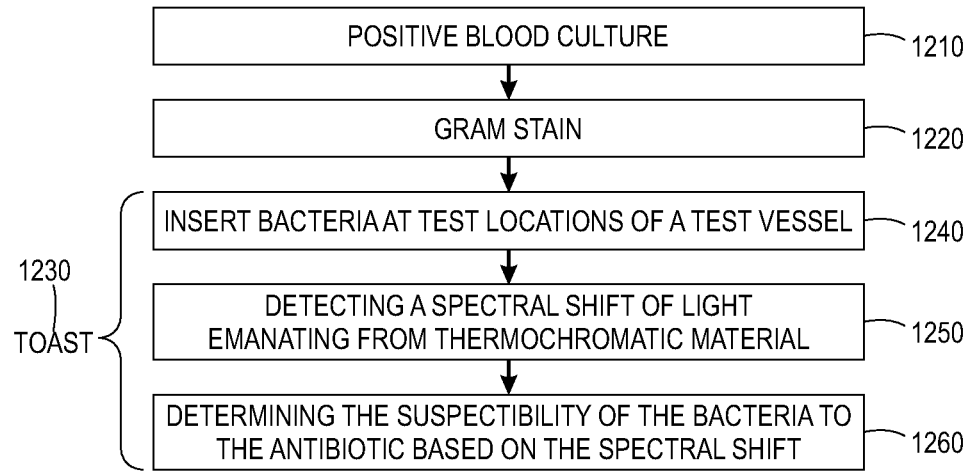
FIGS. 12A and 12B are flow diagrams illustrating processes for thermo-optical antimicrobial susceptibility testing (TOAST) using thermochromic sensing in accordance with some embodiments.

Current testing of significant bacterial isolates takes between 12 and 24 hours to detect possible drug resistance in common pathogens. The thermochromic sensing approaches discussed herein use optical calorimetry to monitor the temperature of incubation vessels, e.g., incubation test wells, and thereby to determine the growth of pathogen cultures. The disclosed approaches can speed up AST by significantly increasing the detection sensitivity providing the ability to monitor bacterial growth (or its absence) in real time rather than by end-point measurements. In some embodiments, use of the thermochromic sensing techniques described herein can reduce the time needed to obtain the minimum inhibitory concentration of antibiotic by more than 60%, more than 70% or even more than 80% when compared to current approaches. FIG. 12A is a flow diagram illustrating a process for thermo-optical antimicrobial susceptibility testing using thermochromic sensing in accordance with some embodiments. After a patient sample is flagged as positive for growth by a blood culture instrument (1210), an aliquot of the sample is subjected to Gram staining (1220) to identify the bacteria as Gram-negative or Gram-positive. After separation from the blood culture medium, and suspension at an appropriate concentration, the bacteria are introduced to test vessels for TOAST (1230). Bacteria is cultured 1240 in a medium at test locations of a test vessel, wherein different test locations contain different types, concentrations and/or combinations of antibiotic. A thermochromic material is disposed at the test locations and is thermally coupled to sense energy conversion of the bacteria. A spectral shift of the light emanating from the thermochromic material at each of the test locations is detected 1250. The susceptibility of the bacteria to the different types, concentrations and/or combinations of antibiotic is determined 1260 based on the spectral shift.

Figure 12B:
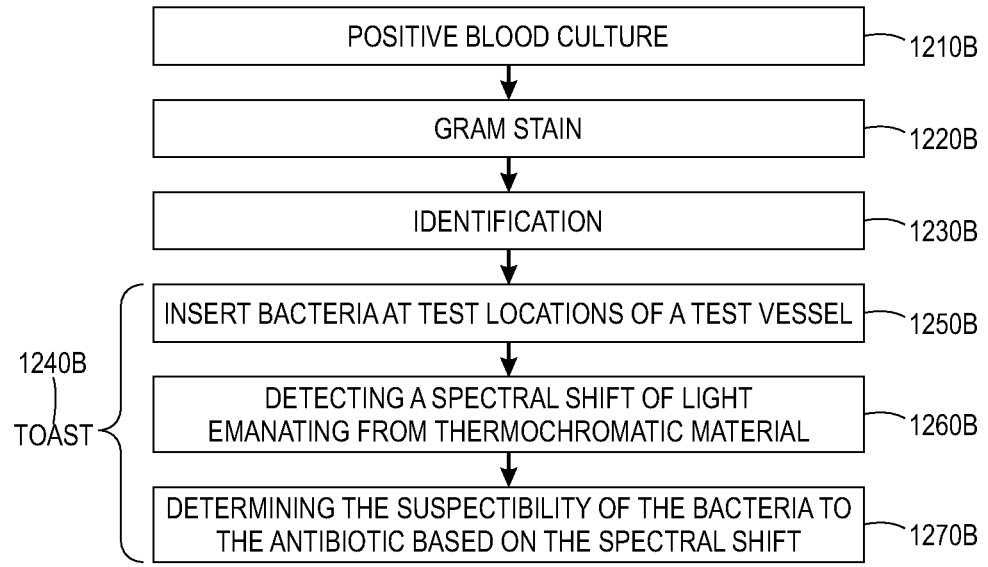

FIG. 12B is a flow diagram illustrating a process for using thermochromic sensing in accordance with some embodiments. After a patient sample is flagged as positive for growth by a blood culture instrument (1210*b*), an aliquot of the sample is subjected to Gram staining (1220*b*) to identify the bacteria as Gram-negative or Gram-positive. The culture is subjected to identification testing (1230*b*) for example via standard biochemical tests or rapid mass spectrometry methods. Following identification of the bacteria, the bacteria are introduced to test vessels for TOAST (1240*b*). Bacteria are cultured 1250*b* in a medium at test locations of a test vessel, wherein different test locations contain different types, concentrations and/or combinations of antibiotic. A thermochromic material is disposed at the test locations and is thermally coupled to sense energy conversion of the bacteria. A spectral shift of the light emanating from the thermochromic material at each of the test locations is detected 1260*b*. The susceptibility of the bacteria to the different types, concentrations and/or combinations of antibiotic is determined 1270*b* based on the spectral shift.

Figure 13A:
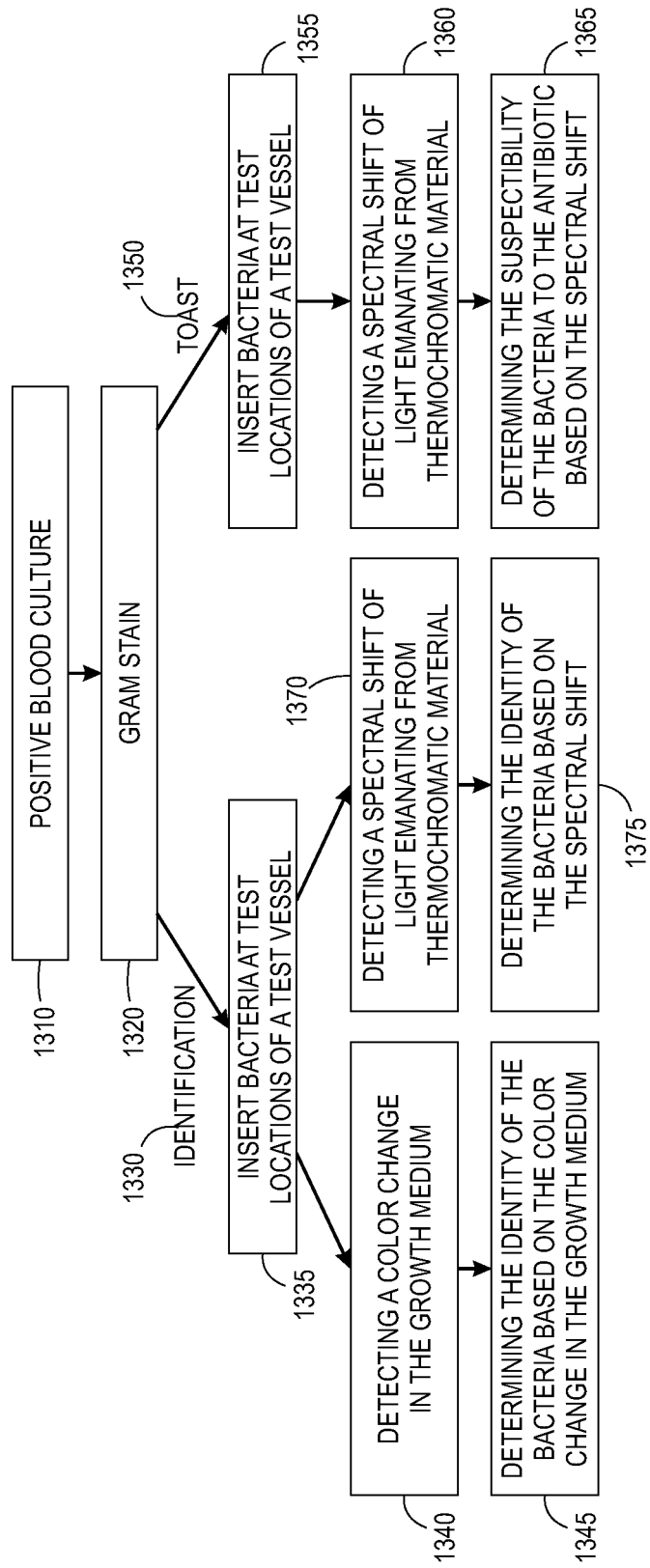
FIGS. 13A through 13C are flow diagrams illustrating processes for bacteria identification and thermo-optical antimicrobial susceptibility testing using thermochromic sensing in accordance with some embodiments.

FIG. 13A is a flow diagram illustrating a process for bacteria identification and thermo-optical antimicrobial susceptibility testing using thermochromic sensing in accordance with some embodiments. After a patient sample is flagged as positive for growth by a blood culture instrument (1310), an aliquot of the sample is subjected to Gram staining (1320) to identify the bacteria as Gram-negative or Gram-positive. After separation from the blood culture medium, and suspension at an appropriate concentration, the bacteria are introduced to test vessels for identification (1330) and for TOAST (1350). For identification 1330, bacteria is cultured 1335 in a medium at test locations of a test vessel, wherein different test locations contain different types, concentrations and/or combinations of test substance and indicator substance. A thermochromic material is disposed at the test locations and is thermally coupled to sense energy conversion of the bacteria. A spectral shift of the light emanating from the thermochromic material at each of the test locations is detected 1370. The identification of the bacteria is determined 1375 based on the spectral shift for example as explained in the description of FIG. 8. In addition, the color change in the growth medium resulting from incubation of bacteria in the presence of the test substance and indicator substance is detected 1340. The identification of the bacteria is determined 1345 based on the color change in the growth medium. For TOAST 1350, bacteria are cultured 1355 in a medium at test locations of a test vessel, wherein different test locations contain different types, concentrations and/or combinations of antibiotic. A thermochromic material is disposed at the test locations and is thermally coupled to sense energy conversion of the bacteria. A spectral shift of the light emanating from the thermochromic material at each of the test locations is detected 1360. The susceptibility of the bacteria to the different types, concentrations and/or combinations of antibiotic is determined 1365 based on the spectral shift.

Figure 13B:
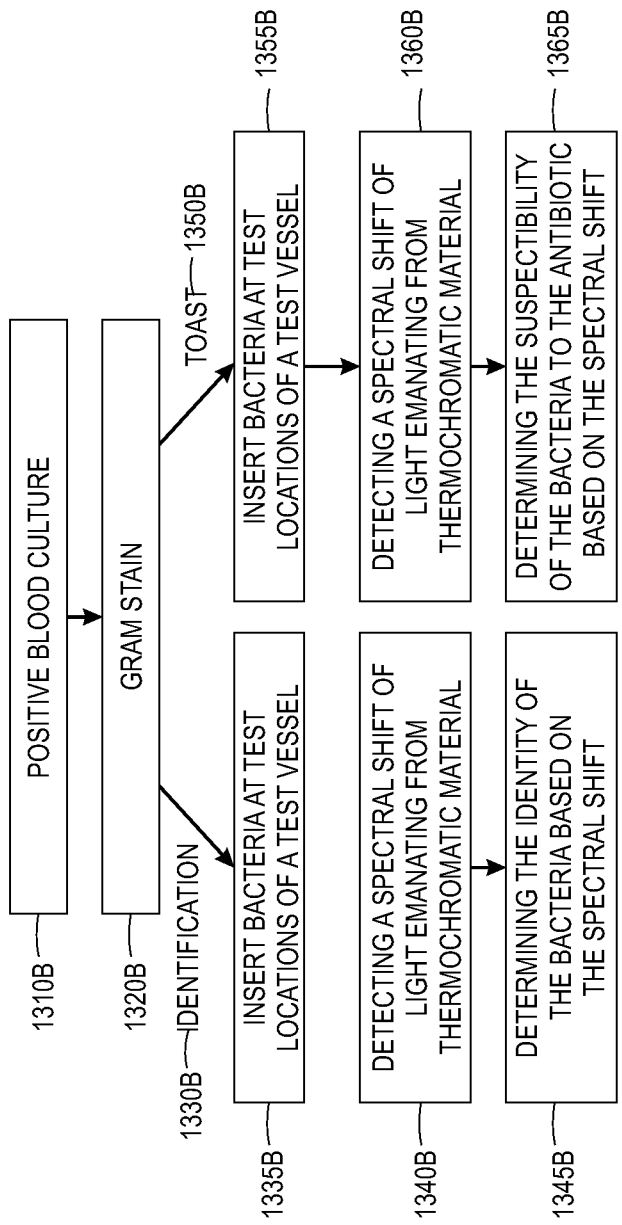

FIG. 13B is a flow diagram illustrating a process for bacteria identification and thermo-optical antimicrobial susceptibility testing using thermochromic sensing in accordance with some embodiments. After a patient sample is flagged as positive for growth by a blood culture instrument (1310*b*), an aliquot of the sample is subjected to Gram staining (1320*b*) to identify the bacteria as Gram-negative or Gram-positive. After separation from the blood culture medium, and suspension at an appropriate concentration, the bacteria are introduced to test vessels for identification (1330b) and for antimicrobial susceptibility testing TOAST (1350b). For identification, bacteria are cultured 1335b in a medium at test locations of a test vessel, wherein different test locations contain different types, concentrations and/or combinations of test substance and indicator substance. A thermochromic material is disposed at the test locations and is thermally coupled to sense energy conversion of the bacteria. A spectral shift of the light emanating from the thermochromic material at each of the test locations is detected 1340b. The identification of the bacteria is determined 1345b based on the spectral shift. For TOAST, bacteria are cultured 1355b in a medium at test locations of a test vessel, wherein different test locations contain different types, concentrations and/or combinations of antibiotic. A thermochromic material is disposed at the test locations and is thermally coupled to sense energy conversion of the bacteria. A spectral shift of the light emanating from the thermochromic material at each of the test locations is detected 1360b. The susceptibility of the bacteria to the different types, concentrations and/or combinations of antibiotic is determined 1365b based on the spectral shift.

Figure 13C:
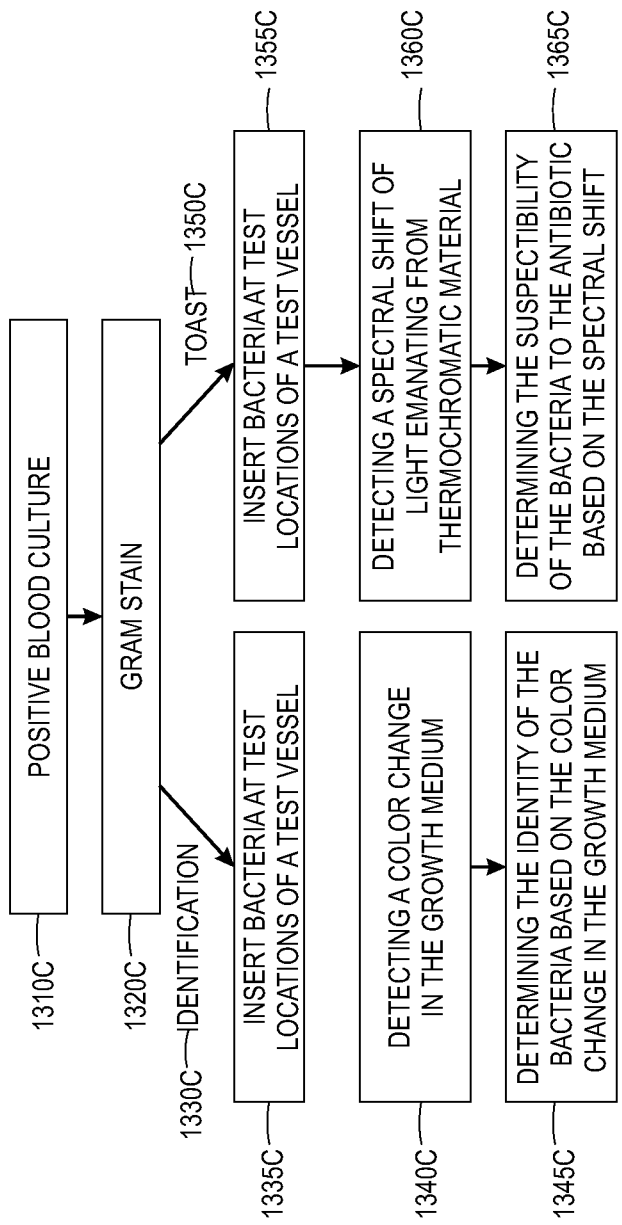

FIG. 13C is a flow diagram illustrating a process for bacteria identification and thermo-optical antimicrobial susceptibility testing using thermochromic sensing in accordance with some embodiments. After a patient sample is flagged as positive for growth by a blood culture instrument (1310c), an aliquot of the sample is subjected to Gram staining (1320c) to identify the bacteria as Gram-negative or Gram-positive. After separation from the blood culture medium, and suspension at an appropriate concentration, the bacteria are introduced to test vessels for identification (1330c) and for TOAST (1350c). For identification, bacteria are cultured 1335c in a medium at test locations of a test vessel, wherein different test locations contain different types, concentrations and/or combinations of test substance and indicator substance. The color change in the growth medium resulting from incubation of bacteria in the presence of the test substance and indicator substance is detected 1340c. The identification of the bacteria is determined 1345c based on the color change in the growth medium. For TOAST, bacteria are cultured 1355c in a medium at test locations of a test vessel, wherein different test locations contain different types, concentrations and/or combinations of antibiotic. A thermochromic material is disposed at the test locations and is thermally coupled to sense energy conversion of the bacteria. A spectral shift of the light emanating from the thermochromic material at each of the test locations is detected 1360c. The susceptibility of the bacteria to the different types, concentrations and/or combinations of antibiotic is determined 1365c based on the spectral shift.

Figure 14A:
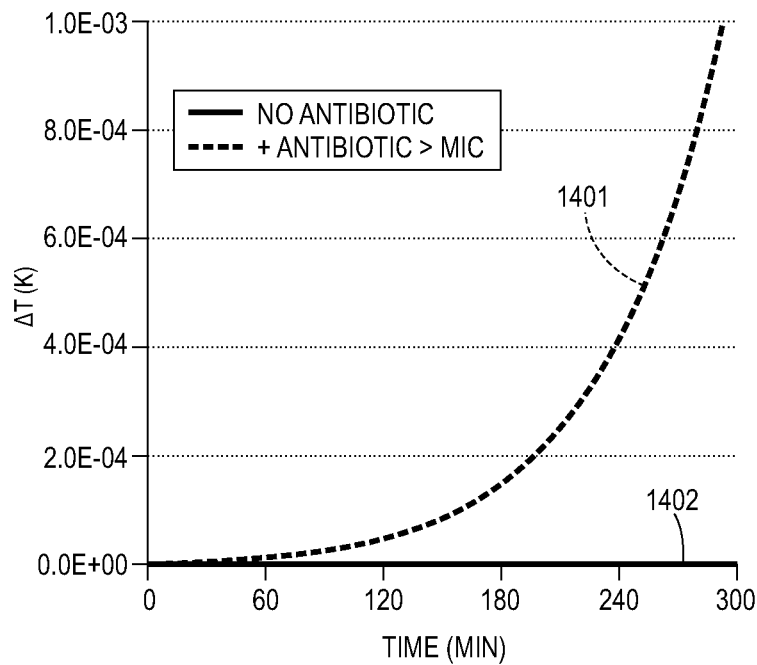
FIG. 14A shows graphs that illustrate the simulated change in temperature $\Delta T$ (K) with respect to time for a growing *E. coli* colony with no antibiotic and with a minimum inhibitory concentration of antibiotic over a the range of thermionic sensing using the wavelength shift detector discussed in FIG. 10A.

Bacteria generate on the order of 2 pW per cell when alive. Thriving pathogen cultures accordingly increase their energy conversion over time due to culture growth by mitosis or other replication mechanisms. Inhibited or declining energy conversion output of cultures indicates culture death. In antimicrobial susceptibility testing, inhibited or declining energy conversion output of culture is related to the efficacy of antimicrobial drugs. Thermochromic sensing using the thermochromic sensing test vessel described in connection test vessels and/or wavelength shift detectors described herein can resolve changes in wavelength of $\Delta\lambda \approx 3$ fm at a sampling rate of about 100 Hz which provides a resolution for temperature change of about 60 nanoKelvin (nK). The temperature measurement bandwidth when using thermochromic materials that exhibit spectral shifts of 50 nm/K sampled with 14 bit resolution is about 1 milliKelvin (mK). FIG. 14A shows graphs that illustrate the change in temperature $\Delta T$ (K) with respect to time for a growing *E. coli* colony with no antibiotic (graph 1401) and with a minimum inhibitory concentration (MIC) of antibiotic (graph 1402) over a the range of 1 mK (about 290 minutes) of thermochromic sensing using the wavelength shift detectors discussed herein. The total test volume is assumed to be 0.1 ml and the initial bacteria concentration is assumed to be 500000 colony forming units per ml (cfu/ml).

Figure 14B:
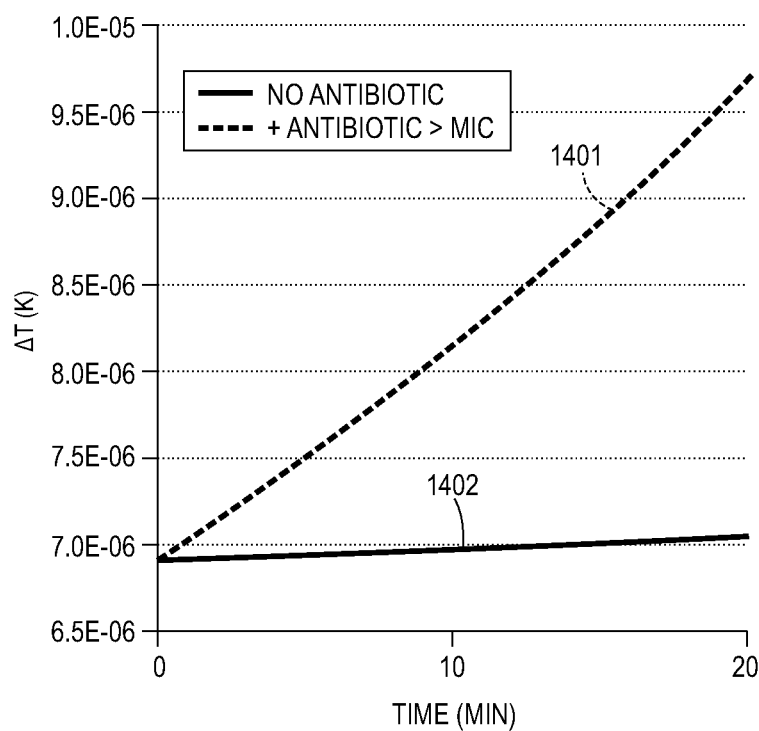
FIG. 14B shows a portion of the graphs of FIG. 14A corresponding to the first 20 minutes of colony growth and indicating the measurement resolution achievable using the wavelength shift detector discussed in FIG. 10A.

FIG. 14B shows a portion of the graphs 1401, 1402 corresponding to the first 20 minutes of colony growth. The gridlines along the $\Delta T$ axis of FIG. 14B indicate the 60 nK resolution of the wavelength shift detector. Thus, it will be appreciated from the graphs of FIG. 14B about the first 10 to 20 minutes of testing using the approaches disclosed herein can indicate growth trends sufficient to identify the MIC for antimicrobial testing. Specifically, uninhibited colony growth results in an exponential increase in temperature of the test site. An increasing temperature in a test site therefore indicates a thriving bacteria colony and can be used as a temperature reference to compare inhibited growth to. Inhibited colony growth will result in smaller temperature increases or in constant temperature when no growth at all occurs. Test sites with inhibited and uninhibited growth of live substance can therefore be identified by their differential temperature development over time. Test wells with live substance but without growth inhibitors will therefore serve as positive control sites in some embodiments. During an antimicrobial susceptibility test, different test sites with different antimicrobial drugs may show effects of the drug at different times. One drug may act faster on the microbes than a second drug, although both drugs may be effective in inhibiting the bacterium colony of interest. Therefore, a continuous reporting of temperatures at different test sites may inform about the efficacy of a particular drug earlier than about the efficacy of a second drug or the efficacy of a second concentration of the first drug. Consequently, a continuous reporting of differential temperature of test sites may serve a continuous representation of cell viability at that test site. Unlike an end-point measurement, such a reporting system can continuously update any user for example about the currently best performing test substance. In clinical practice, a physician could be informed by a TOAST system in an automated manner, for example by email or text message, that the first effective drug for a particular patient has been identified, if the energy conversion in the corresponding well has been continuously low for a prolonged time. Simultaneously, ambient temperature, even within the temperature controlled environment of an incubator, may drift significantly compared to the temperature increase of the test site. In some embodiments negative control sites or wells without live substance will be used to assess the ambient temperature drift.

To assess the efficacy of a test substance inhibiting live substance growth, including but not limited to bacterial growth, the temperature development of test locations is monitored over time. After initial insertion of the test plate into the full incubation and read-out system it is expected that temperatures will fluctuate strongly and that initial temperature reading will be ignored. After sufficient temperature stabilization, positive control locations show temperature changes for example as the ones shown in 1401. Test locations with test substances that effectively inhibit growth of the live substance show temperature developments as depicted in 1402. Test substances that not only inhibit the growth but produce cytotoxic or germicidal effects so that necrosis or apoptosis or any other form of death or reduction in metabolism of the live substance is induced will result in a temperature decrease of the test location compared with the positive control location. The temperature change over time will generally fall between the ones of positive control locations and negative control locations. Several metrics for determining the response of the live matter to the test substance can be used. As a simple non-limiting example the absolute value of temperature difference between a positive control location and a test location remains below a certain threshold value, for example 10 µK during the course of the experimental duration to determine uninhibited growth of the test substance at a test location. Alternatively, the same thresholding calculation could be performed by averaging the temperature of several positive control locations. Another example for a metric of inhibited or uninhibited growth may be a temperature difference that is normalized by the absolute temperature of control locations. Another example for a metric may be the consideration of the temperature derivatives with respect to time. Another example for evaluation procedures may be a curve fit, for example an exponential growth fit to the temperature-time development data. Individual fit parameters for control and test location may then be used for evaluating the growth or the lack thereof of live substance in test locations. It will be appreciated that these are merely examples of possible data evaluation concepts that can be used in order to extract meaningful information from the fundamental data generated in a TOAST system. Depending on the live matter and the actual intent of a particular test these concepts or others may be utilized.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Various modifications and alterations of the embodiments discussed above will be apparent to those skilled in the art, and it should be understood that this disclosure is not limited to the illustrative embodiments set forth herein. The reader should assume that features of one disclosed embodiment can also be applied to all other disclosed embodiments unless otherwise indicated. It should also be understood that all U.S. patents, patent applications, patent application publications, and other patent and non-patent documents referred to herein are incorporated by reference, to the extent they do not contradict the foregoing disclosure.

What is claimed is:

1. A device comprising:
   a test vessel comprising a base material of low heat conductivity material and having one or more test locations, each test location being thermally isolated from transferring heat into the test vessel and configured to contain a medium for culturing a live substance;
   a thermochromic material thermally coupled to the one or more test locations, the thermochromic material configured to exhibit a spectral shift in light emanating from the thermochromic material in response to a change in temperature of the thermochromic material, the spectral shift occurring in response to an increase or decrease in a metabolism of the live substance; and
   at least one material layer disposed at the one or more test locations and configured to enhance sensitivity of thermochromic sensing of the test locations.

2. The device of claim 1, wherein the at least one material layer comprises a heat conducting layer disposed between the thermochromic material and the medium, the heat conducting layer configured to enhance sensitivity of the thermochromic sensing due to an improved heat conductivity from one or both of the medium and the live substance to the thermochromic material.

3. The device of claim 2, wherein the heat conducting layer comprises one or more of indium tin oxide (ITO), metal, diamond, zinc oxide, graphene, graphite, and indium phosphide.

4. The device of claim 1, wherein the at least one material layer comprises a heat insulating layer disposed between the thermochromic material and the base material of the test vessel, the heat insulating layer configured to enhance sensitivity of the thermochromic sensing due to reduced heat conductivity from the thermochromic material to an ambient equilibrium temperature.

5. The device of claim 1, wherein the at least one material layer comprises a light absorbing layer configured to enhance a signal to noise ratio of thermochromic sensing by reducing a component of a detector signal produced by non-signal light, wherein non-signal light is light other than light emanating from the thermochromic material.

6. The device of claim 1, comprising a sterile coating disposed over the thermochromic material such that the thermochromic material is positioned between a bottom surface of the test locations and the sterile coating.

7. The device of claim 6, wherein the sterile coating comprises one or more of parylene, indium tin oxide (ITO), metal, polyethylene glycol (PEG), diamond, zinc oxide, graphene, graphite, and indium phosphide.

8. The device of claim 1, wherein the spectral shift in the light emanating from the thermochromic material comprises a spectral shift in at least one of scattered, reflected, and fluorescent light emanating from the thermochromic material.

9. The device of claim 8, wherein:
   the light emanating from the thermochromic material is in response to measurement light that interacts with the thermochromic material; and
   the vessel, at least at the test locations, is optically transmissive to one or more of the scattered light, the reflected light, the fluorescent light, and the measurement light.

10. The device of claim 1, wherein the thermochromic material comprises one or more of thermochromic liquid crystals, leuco dye, a fluorophore, Prodan bound to DPPC, or a fluorescent protein.

11. The device of claim 1, wherein the light emanating from the thermochromic material is configured to exhibit a spectral shift as a function of temperature in a range of about 0.5 nm/K to about 1000 nm/K.

12. A kit, comprising:
   a sterile test vessel comprising a base material of low heat conductivity material and having multiple test locations, each test location being thermally isolated from transferring heat into the test vessel;
   a medium contained by the test vessel at the test locations, the medium suitable for culturing a live substance; and
   a thermochromic material thermally coupled to the test locations, the thermochromic material configured to exhibit a spectral shift in light emanating from the thermochromic material in response to a sub-Kelvin change in temperature of the thermochromic material, the spectral shift occurring in response to an increase or decrease in a metabolism of the live substance; and at least one material layer disposed at the test locations and configured to enhance sensitivity of thermochromic sensing of the test locations.

13. The kit of claim 12, wherein the at least one material layer comprises a heat conducting layer disposed between the thermochromic material and the medium, the heat conducting layer configured to enhance sensitivity of the thermochromic sensing due to an improved heat conductivity from the medium and/or the live substance to the thermochromic material.

14. The kit of claim 13, wherein the heat conducting layer comprises one or more of indium tin oxide (ITO), metal, diamond, zinc oxide, graphene, graphite, and indium phosphide.

15. The kit of claim 12, wherein the at least one material layer comprises a heat insulating layer disposed between the thermochromic material and the base material of the test vessel, the heat insulating layer configured to enhance sensitivity of the thermochromic sensing due to reduced heat conductivity from the thermochromic material to an ambient equilibrium temperature.

16. The kit of claim 12, wherein the at least one material layer comprises a light absorbing layer configured to enhance a signal to noise ratio of thermochromic sensing by reducing a component of a detector signal produced by non-signal light, wherein non-signal light is light other than light emanating from the thermochromic material.

17. The kit of claim 12, comprising a sterile coating disposed over the thermochromic material so that the thermochromic material is positioned between a bottom surface of the test locations and the sterile coating.

18. The kit of claim 17, wherein the sterile coating comprises one or more of parylene, indium tin oxide (ITO), metal, polyethylene glycol (PEG), diamond, zinc oxide, graphene, graphite, and indium phosphide.

19. The kit of claim 12, further comprising one or more test substances at the one or more test locations.

20. The kit of claim 19, wherein the one or more test substances comprise different types, different amounts, and different combinations of drugs at the test locations.

* * * * *